United States Patent
Hudson et al.

(10) Patent No.: US 12,371,653 B2
(45) Date of Patent: Jul. 29, 2025

(54) EXTRACELLULAR VESICLES AS BIOMARKERS AND THERAPEUTICS FOR NEUROMUSCULAR DISORDERS

(71) Applicants: University of Delaware, Newark, DE (US); Iowa State University Research Foundation, Inc., Ames, IA (US)

(72) Inventors: Matthew B. Hudson, Media, PA (US); Joshua T. Selsby, Ames, IA (US)

(73) Assignees: University of Delaware, Newark, DE (US); Iowa State University Research Foundation, Inc., Ames, IA (US)

( * ) Notice: Subject to any disclaimer, the term of this patent is extended or adjusted under 35 U.S.C. 154(b) by 972 days.

(21) Appl. No.: 17/270,674

(22) PCT Filed: Aug. 23, 2019

(86) PCT No.: PCT/US2019/047943
§ 371 (c)(1),
(2) Date: Feb. 23, 2021

(87) PCT Pub. No.: WO2020/041725
PCT Pub. Date: Feb. 27, 2020

(65) Prior Publication Data
US 2021/0348114 A1    Nov. 11, 2021

Related U.S. Application Data

(60) Provisional application No. 62/722,331, filed on Aug. 24, 2018.

(51) Int. Cl.
*C12N 1/02* (2006.01)
*C12Q 1/6883* (2018.01)
*G01N 33/68* (2006.01)

(52) U.S. Cl.
CPC ............ *C12N 1/02* (2013.01); *C12Q 1/6883* (2013.01); *G01N 33/6803* (2013.01); *G01N 33/6887* (2013.01); *G01N 2800/10* (2013.01)

(58) Field of Classification Search
CPC .... C12N 1/02; C12Q 1/6883; G01N 33/6803; G01N 33/6887; G01N 2800/10; G01N 2800/01
See application file for complete search history.

(56) References Cited

U.S. PATENT DOCUMENTS

2016/0363599 A1    12/2016    Goetzl

FOREIGN PATENT DOCUMENTS

| WO | WO-2013084000 A2 | * | 6/2013 | ............ | A61K 35/36 |
| WO | 2014014087 A1 | | 1/2014 | | |
| WO | 2015002956 A1 | | 1/2015 | | |
| WO | 2016179091 A1 | | 11/2016 | | |
| WO | WO-2017054086 A1 | * | 4/2017 | ............ | A61K 31/713 |
| WO | WO-2017203260 A1 | * | 11/2017 | ............ | A61K 35/12 |

OTHER PUBLICATIONS

Aguilar et al., (Cell Death Discov., 4(33): 1-11 (2018) (Year: 2018).*
Goodacre et al., mBio, 5(1): e00744-13 (2013) (Year: 2013).*
Koutsoulidou et al., Human Mol. Gen., 26(17):3285-3302 (2017) (Year: 2017).*
Yang et al., PLoS One 4(6):e6074 (2009) (Year: 2009).*
Consalvi et al., Stem Cells Internat., 6093601:1-11 (2016) (Year: 2016).*
Cetin et al., Front. Mol. Neurosci., 13(581097):1-14 (2020) (Year: 2020).*
Millar et al.. Mol. Membrane Biol., 25(4):279-292 (2008) (Year: 2008).*
Forterre et al., Cell Cycle, 13(1):78-89 (2014) (Year: 2014).*
Stickney et al., Biochem. Biophys. Res. Comm., 472:53-59 (2016) (Year: 2016).*
Zanotti et al., Matrix Biol., 74:77-100 (2018) (Year: 2018).*
Aminzadeh et al., Stem Cell Reports, 10:942-955 (2018) (Year: 2018).*
Jarmin et al., Expert Opin. Biol. Ther., 14(2):209-230 (2014) (Year: 2014).*
Bellavia et al., Theranostics, 7(5):1333-1345 (2013) (Year: 2013).*
Gilligan et al., Int. J. Mol. Sci., 18(1122):1-12 (2017) (Year: 2017).*
Ohno et al., Mol. Ther., 21(1):185-191 (2013) (Year: 2013).*
Schiller et al., Mol. Ther. Meth. & Clini. Devel., 9:278-287 (2018) (Year: 2018).*
"Extended European Search Report corresponding to European Application No. 19852933.1 dated Apr. 21, 2022".
Aminzadeh, Mark A., et al., "Exosome-Mediated Benefits of Cell Therapy in Mouse and Human Models of Duchenne Muscular Dystrophy", Stem Cell Reports 10(3):942-955 (Mar. 13, 2018).
Bier, Ariel, et al., "Placenta-derived mesenchymal stromal cells and their exosomes exert therapeutic effects in Duchenne muscular dystrophy", Biomaterials 174:67-78 (May 3, 2018).
"International Preliminary Report corresponding to International Application No. PCT/US2019/047943 mailed Mar. 11, 2021".
"International Search Report and Written Opinion corresponding to International Application No. PCT/US2019/047943 mailed Dec. 17, 2019".
Matsuzaka, Yasunari , et al., "Characterization and Functional Analysis of Extracellular Vesicles and Muscle-Abundant miRNAs (miR-1, miR-133a, and miR-206) in C2C12 Myocytes and mdx Mice", PLOS One 11:12(e0167811 (pp. 1-23) (Dec. 15, 2016.

* cited by examiner

*Primary Examiner* — Kade Ariani

(74) *Attorney, Agent, or Firm* — Myers Bigel, P.A.

(57) ABSTRACT

This invention relates to extracellular vesicles and method of isolated tissue-specific extracellular vesicles from bodily fluids. The invention further relates to methods of using extracellular vesicles for diagnostic applications for detecting and monitoring diseases, conditions, and damage in a subject. The invention also relates to methods of using extracellular vesicles for therapeutic applications for treating diseases, conditions, and damage in a subject.

11 Claims, 15 Drawing Sheets

A

B

C

D

E

F

A

B

EXTRACELLULAR VESICLES AS BIOMARKERS AND THERAPEUTICS FOR NEUROMUSCULAR DISORDERS

STATEMENT OF PRIORITY

This application is a 35 U.S.C. § 371 national phase application of PCT Application PCT/US2019/047943 filed Aug. 23, 2019, which claims the benefit, under 35 U.S.C. § 119(e), of U.S. Provisional Applications No. 62/722,331, filed on Aug. 24, 2018, the entire contents of each of which are incorporated by reference herein in its entirety.

FIELD OF THE INVENTION

This invention relates to extracellular vesicles and method of isolated tissue-specific extracellular vesicles from bodily fluids. The invention further relates to methods of using extracellular vesicles for diagnostic applications for detecting and monitoring diseases, conditions, and damage in a subject. The invention also relates to methods of using extracellular vesicles for therapeutic applications for treating diseases, conditions, and damage in a subject.

BACKGROUND OF THE INVENTION

Extracellular vesicles (EVs) are lipid vesicles released from cells into the extracellular environment and are found in most, if not all, biological fluids. EVs contain a variety of molecular cargo from the originating cell and contribute to paracrine and endocrine signaling by delivering cargo into neighboring and distant cells. A major limitation to utilizing EVs as biomarkers or for therapeutic delivery is that most, if not all, tissues release EVs into bodily fluids. Thus, EVs in bodily fluids originate from a variety of tissues in the body, making it impossible to determine what tissue they originated from or what tissue they will deliver cargo to.

The present invention overcomes shortcomings in the art by providing methods for isolating EVs from bodily fluids that originated from specific tissues and methods of using EVs for detection, monitoring, and treatment of disorders.

SUMMARY OF THE INVENTION

The present invention is based, in part, on the development of methods for isolating EVs from bodily fluids that originated from specific tissues, e.g., muscle tissue. The invention further relates to methods of detecting and monitoring neuromuscular disorders by isolating tissue-derived (e.g., muscle-derived) EVs and characterizing one or more components of the EVs. The invention additionally relates to methods of using EVs to deliver therapeutic agents to a subject.

Thus, one aspect of the invention relates to a method of isolating muscle-derived extracellular vesicles from a bodily fluid, comprising: a) contacting the bodily fluid with a capture agent that specifically binds to a molecule on the surface of muscle-derived extracellular vesicles to form a capture agent:extracellular vesicle complex; and b) isolating the capture agent:extracellular vesicle complex from the bodily fluid.

A further aspect of the invention relates to a method of isolating extracellular vesicles from a cell culture medium, comprising: a) providing cell culture medium in which cells were grown; b) contacting the cell culture medium with a capture agent that specifically binds to a molecule on the surface of the extracellular vesicles to form a capture agent:extracellular vesicle complex; and c) isolating the capture agent:extracellular vesicle complex from the cell culture medium.

Another aspect of the invention relates to a method of detecting a muscle-related disorder, condition, or damage in a subject, comprising: a) isolating muscle-derived extracellular vesicles from a bodily fluid of the subject; b) characterizing one or more components within or on the extracellular vesicles; and c) detecting a muscle-related disorder, condition, or damage based on the characterization of the one or more components or absence of one or more components within or on the extracellular vesicles.

An additional aspect relates to a method of determining a risk of having a muscle-related disorder, condition, or damage in a subject, comprising: a) isolating muscle-derived extracellular vesicles from a bodily fluid of the subject; b) characterizing one or more components within or on the extracellular vesicles; and c) determining a risk of having a muscle-related disorder, condition, or damage based on the characterization of the one or more components or absence of one or more components within or on the extracellular vesicles.

A further aspect of the invention relates to a method of monitoring progression of a muscle-related disorder, condition, or damage in a subject, comprising: a) isolating muscle-derived extracellular vesicles from a bodily fluid of the subject at two or more time points; b) characterizing one or more components within or on the extracellular vesicles at each time point; and c) monitoring progression of a muscle-related disorder, condition, or damage based on changes in the characteristics of the one or more components or absence of one or more components within or on the extracellular vesicles at each time point.

Another aspect of the invention relates to a method of monitoring effectiveness of a treatment of a muscle-related disorder, condition, or damage in a subject, comprising: a) isolating muscle-derived extracellular vesicles from a bodily fluid of the subject at two or more time points before and/or during treatment; b) characterizing one or more components within or on the extracellular vesicles at each time point; and c) monitoring effectiveness of the treatment of a muscle-related disorder, condition, or damage based on changes in the characteristics of the one or more components or absence of one or more components within or on the extracellular vesicles at each time point.

An additional aspect of the invention relates to a method of identifying an effective therapy for a muscle-related disorder, condition, or damage, comprising: a) providing a candidate therapy to a subject or an in vivo or in vitro model of a muscle-related disorder, condition, or damage; b) isolating muscle-derived extracellular vesicles from cells or tissues of the subject or in vivo or in vitro model at two or more time points before, during, and/or after the candidate therapy and/or comparing a single time point from treated and untreated model experimental units/groups; c) characterizing one or more components within or on the extracellular vesicles at each time point; and d) identifying an effective therapy for the muscle-related disorder, condition, or damage based on changes in the characteristics of the one or more components or absence of one or more components within or on the extracellular vesicles at each time point.

A further aspect of the invention relates to a method of identifying an effective therapeutic agent for a muscle-related disorder, condition, or damage; comprising: a) providing a candidate therapeutic agent to a subject or an in vivo or in vitro model of a muscle-related disorder, condition, or damage; b) isolating muscle-derived extracellular vesicles from cells or tissues of the subject or in vivo or in vitro model at two or more time points before, during, and/or after the providing of the candidate therapeutic agent and/or comparing a single time point from treated and untreated model experimental units/groups; c) characterizing one or more components within or on the extracellular vesicles at each time point; and d) identifying an effective therapeutic agent for the muscle-related disorder, condition, or damage based on changes in the characteristics of the one or more components within the extracellular vesicles at each time point.

Another aspect of the invention relates to a method of treating a disorder, condition, or damage in a subject in need thereof, comprising: a) isolating extracellular vesicles comprising one or more therapeutic agents from cell culture medium of cultured cells; and b) administering a therapeutically effective amount of the extracellular vesicles to the subject; thereby treating the disorder, condition, or damage.

An additional aspect of the invention relates to a composition comprising a capture agent for capturing extracellular vesicles.

A further aspect of the invention relates to a composition comprising extracellular vesicles comprising one or more therapeutic agents, the extracellular vesicles isolated from cell culture medium of cultured cells.

Another aspect of the invention relates to a kit for capturing extracellular vesicles, the kit comprising a capture agent.

These and other aspects of the invention are set forth in more detail in the description of the invention below.

DETAILED DESCRIPTION OF THE INVENTION

Figure 1:
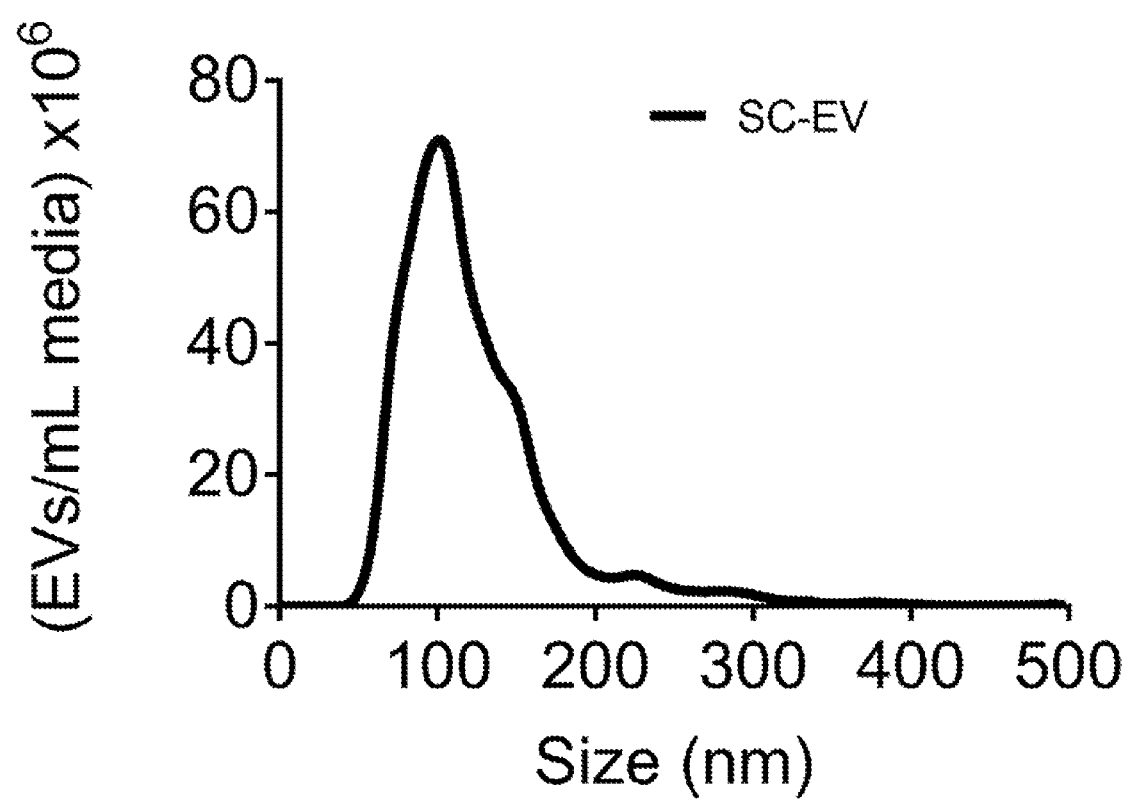
FIG. 1 shows nanoparticle tracking analysis data demonstrating the size distribution and concentration of EVs released during the first 24 hr of SC culture (n=3). An average of $2.00 \times 10^5 \pm 8.04 \times 10^3$ EVs/cell/24 hr. The data demonstrates an average EV size of $125.7 \pm 1.7$ nm with a modal size of $99.3 \pm 2.6$ nm.
Figure 2A:
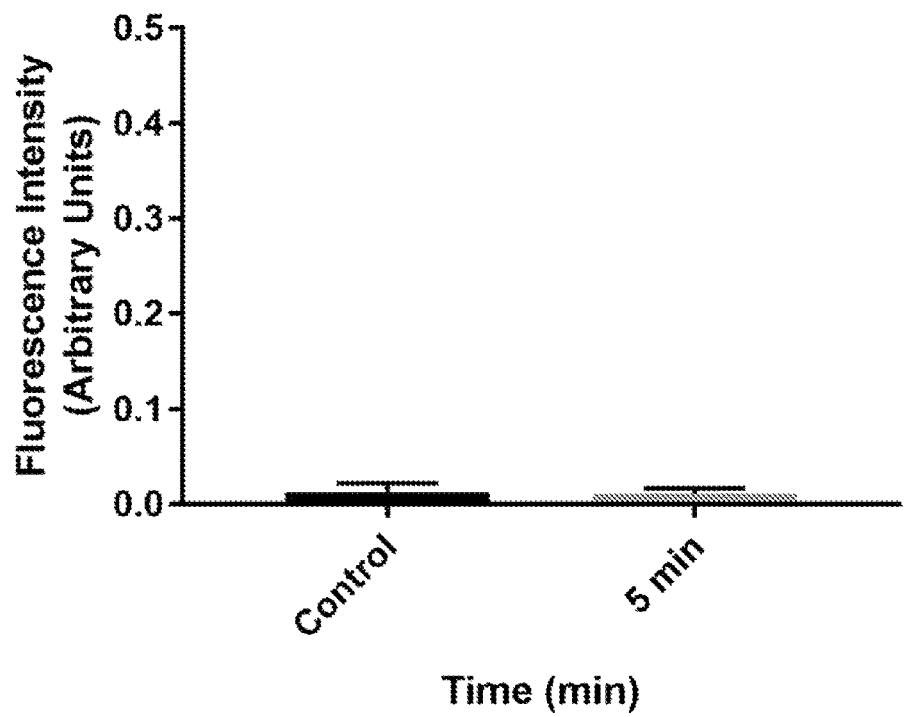
FIGS. 2A-2G show a time course analysis of CFSE-labeled SC-EVs in C2C12 myotubes at (A) 5 min; (B) 30 min; (C) 1 hr; (D) 2 hr; (E) 6 hr; (F) 24 hr; (G) 48 hr of incubation in vitro. * indicates significant difference in fluorescence intensity relative to control.
Figure 2B:
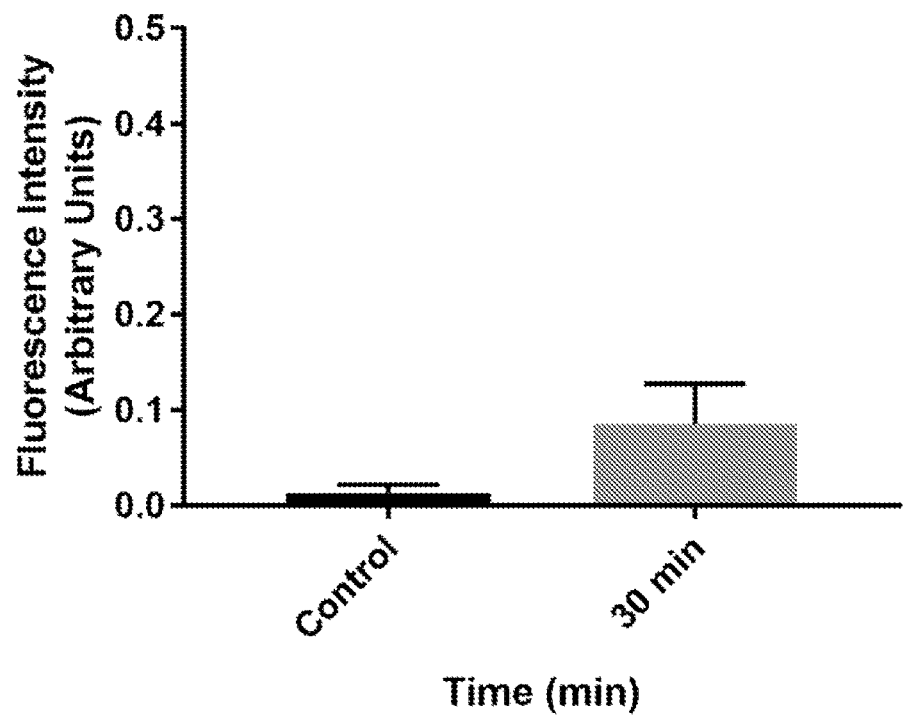
Figure 2C:
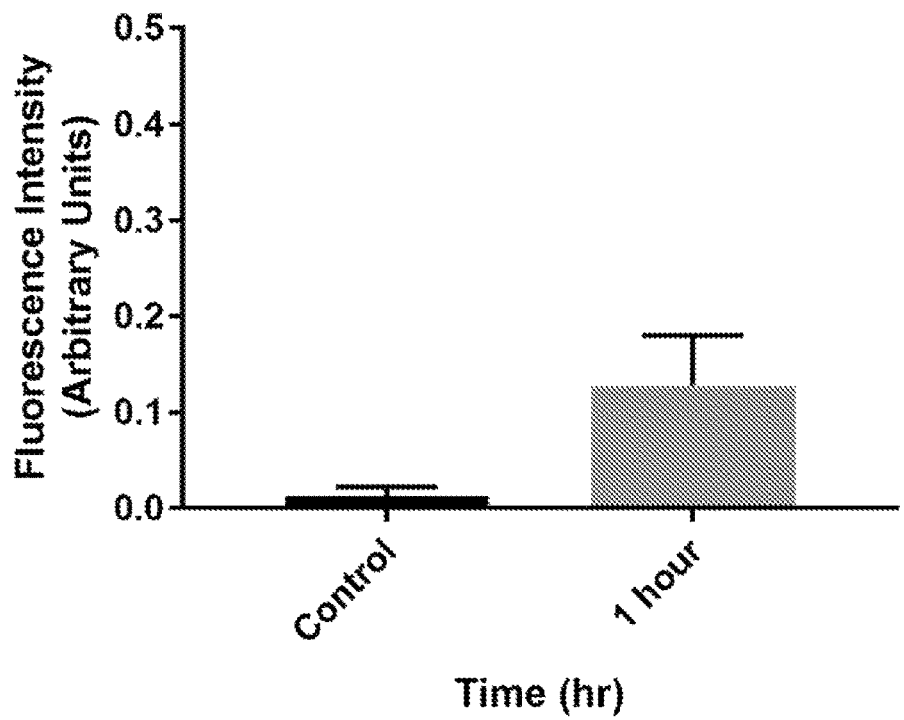
Figure 2D:
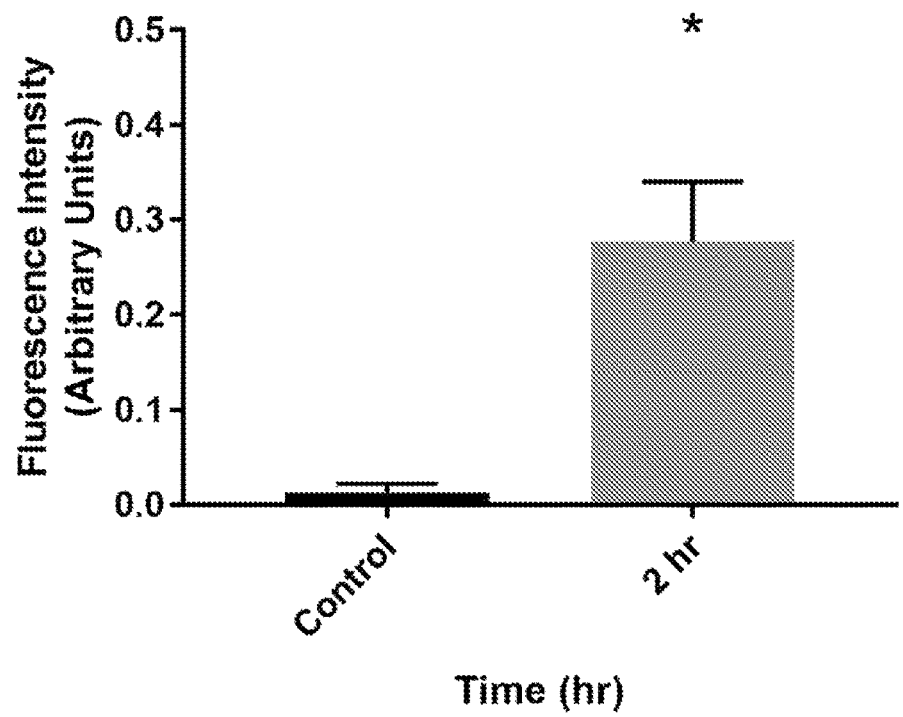
Figure 2E:
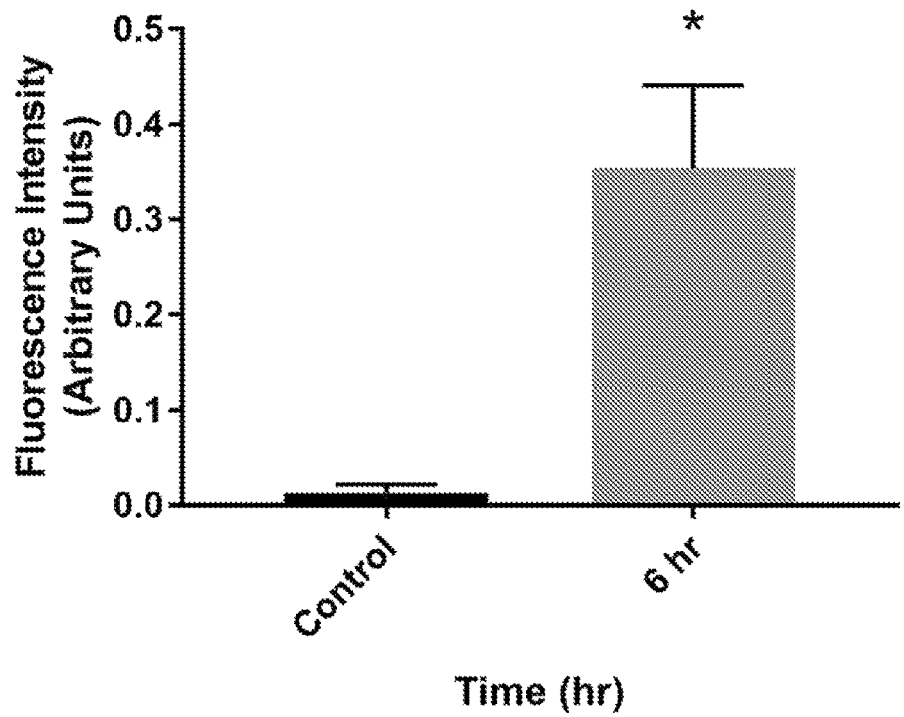
Figure 2F:
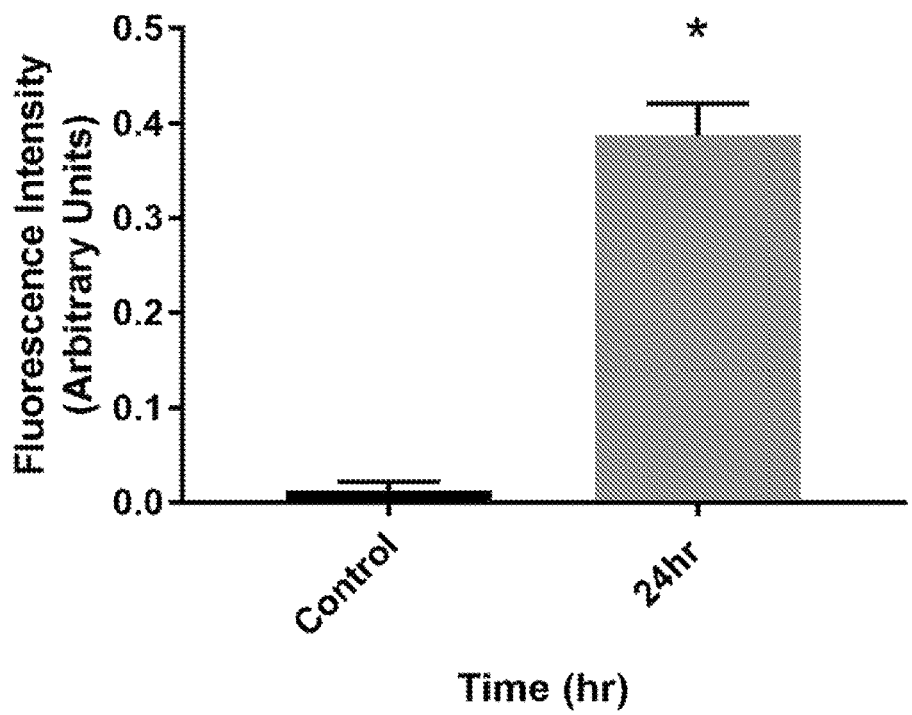
Figure 2G:
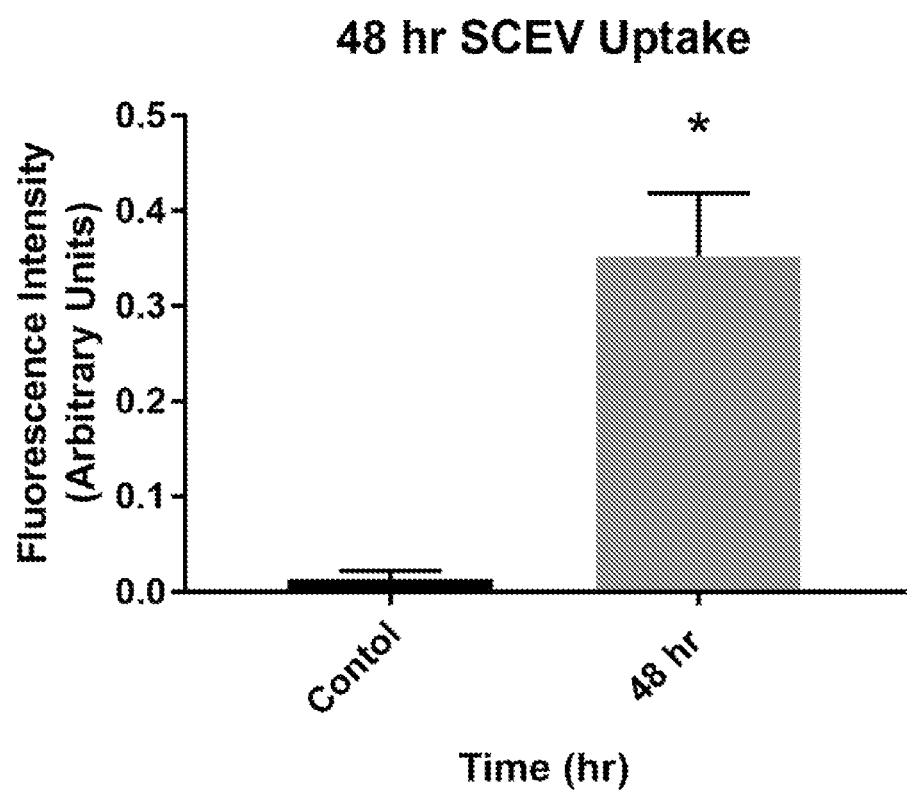
Figure 3A:
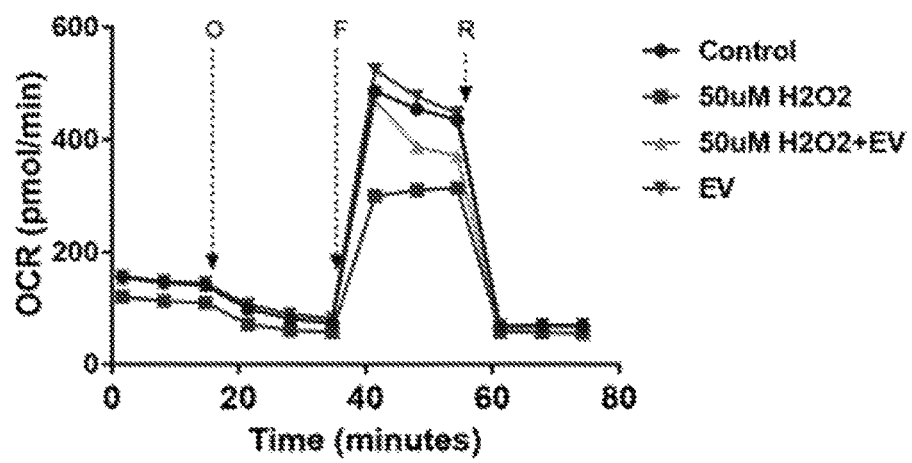
FIGS. 3A-3E show (A) mitochondrial respiration throughout a mitochondrial stress test protocol; (B) Energy map depicting reliance on aerobic vs. glycolytic energy systems as well as overall energetic state of treated cells; (C) Basal respiration of cells in each group; (D) Maximal respiration of each group; (E) Spare respiratory capacity for each group (difference between maximal respiration and basal respiration).
Figure 3B:
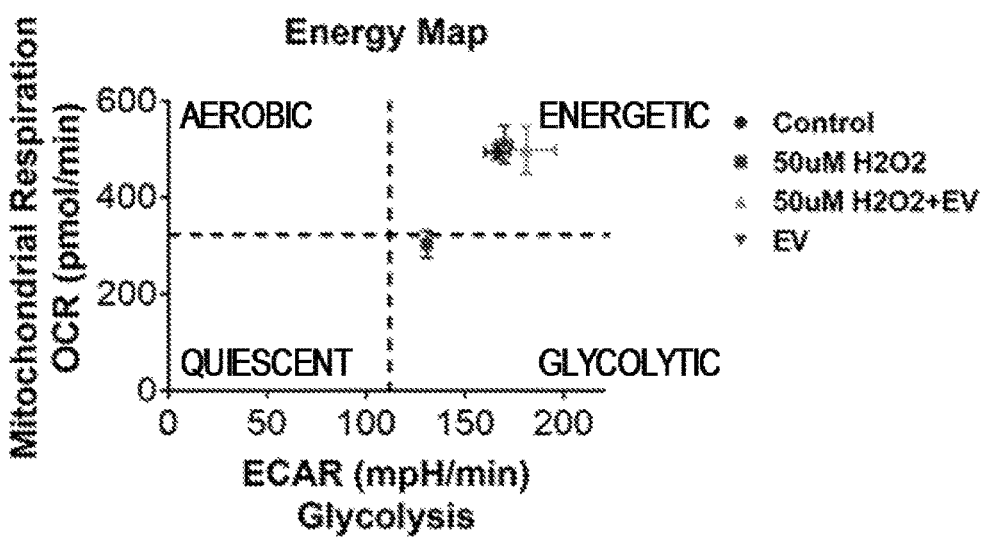
Figure 3C:
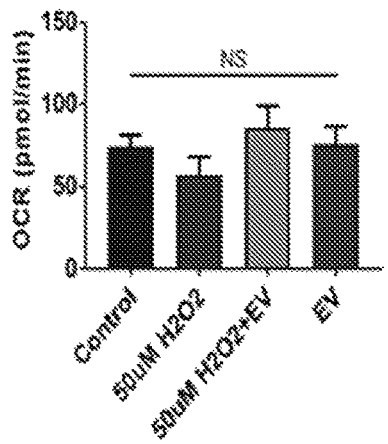
Figure 3D:
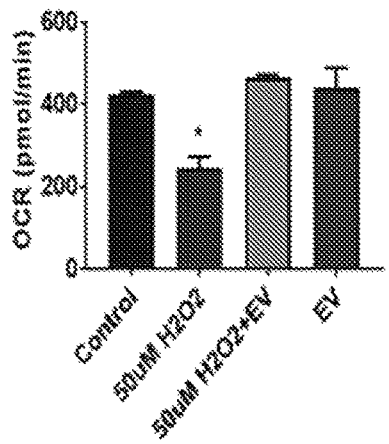
Figure 3E:
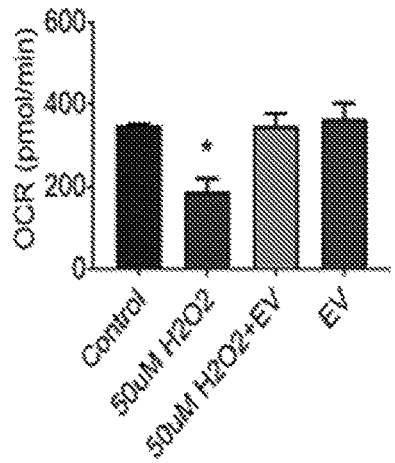

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic genes, polypeptides, antibodies or antigen-binding fragments thereof, manipulation of nucleic acid sequences, production of transformed cells, the construction of vector constructs, and the generation and analysis of datasets. Such techniques are known to those skilled in the art. See, e.g., SAMBROOK et al., MOLECULAR CLONING: A LABORATORY MANUAL 2nd Ed. (Cold Spring Harbor, NY, 2001); F. M. AUSUBEL et al. CURRENT PROTOCOLS IN MOLECULAR BIOLOGY (Green Publishing Associates, Inc. and John Wiley & Sons, Inc., NY).

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

"Optional" or "optionally" means that the subsequently described event or circumstance can or cannot occur, and that the description includes instances where the event or circumstance occurs and instances where it does not.

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or fewer (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or fewer additional nucleotides or amino acids includes the total number of additional nucleotides or amino acids added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in biological activity of at least about 50% or more as compared to the activity of a polypeptide consisting of the recited sequence.

The term "sequence identity," as used herein, has its standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al.,

*Meth. Enzymol.,* 266:460 (1996); blast.wustl/edu/blast/RE-ADME.html. WU-BLAST-2 uses several search parameters, which are preferably set to their default values. The parameters are dynamic values and are established by the program itself depending upon the composition of the particular sequence of interest and the composition of the particular database against which the sequence of interest is being searched; however, the values may be adjusted to increase sensitivity. An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-BLAST-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences that contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations, relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

As used herein, by "isolate" or "purify" (or grammatical equivalents) a virus vector, it is meant that the virus vector is at least partially separated from at least some of the other components in the starting material.

The term "endogenous" refers to a component naturally found in an environment, i.e., a gene, nucleic acid, miRNA, protein, cell, or other natural component expressed in the subject, as distinguished from an introduced component, i.e., an "exogenous" component.

As used herein, the term "heterologous" refers to a nucleotide/polypeptide that originates from a foreign species, or, if from the same species, is substantially modified from its native form in composition and/or genomic locus by deliberate human intervention.

As used herein, the term "nucleic acid" refers to a single or double-stranded polymer of deoxyribonucleotide or ribonucleotide bases read from the 5' to the 3' end. The "nucleic acid" may also optionally contain non-naturally occurring or modified nucleotide bases. The term "nucleotide sequence" or "nucleic acid sequence" refers to both the sense and antisense strands of a nucleic acid, either as individual single strands or in the duplex. The term "ribonucleic acid" (RNA) is inclusive of RNAi (inhibitory RNA), dsRNA (double stranded RNA), siRNA (small interfering RNA), shRNA (short/small hairpin RNA), mRNA (messenger RNA), miRNA (micro-RNA), tRNA (transfer RNA, whether charged or discharged with a corresponding acylated amino acid), long non-coding RNA (lncRNA), ribosomal RNA (rRNA), small nuclear RNA (snRNA), small nucleolar RNA (snoRNA) and cRNA (complementary RNA), and the term "deoxyribonucleic acid" (DNA) is inclusive of cDNA and genomic DNA and DNA-RNA hybrids.

The terms "nucleic acid segment," "nucleotide sequence," or more generally "segment" will be understood by those in the art as functional terms that include genomic sequences, ribosomal RNA sequences, transfer RNA sequences, messenger RNA sequences, small regulatory RNAs, operon sequences and smaller engineered nucleotide sequences that express or may be adapted to express, proteins, polypeptides or peptides. Nucleic acids of the present disclosure may also be synthesized, either completely or in part, by methods known in the art. Thus, all or a portion of the nucleic acids of the present disclosure may be synthesized using codons preferred by a selected host. Such species-preferred codons may be determined, for example, from the codons used most frequently in the proteins expressed in a particular host species. Other modifications of the nucleotide sequences may result in mutants having slightly altered activity.

As used herein with respect to nucleic acids, the term "fragment" refers to a nucleic acid that is reduced in length relative to a reference nucleic acid and that comprises, consists essentially of and/or consists of a nucleotide sequence of contiguous nucleotides identical or almost identical (e.g., 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. In some embodiments, the nucleic acid fragment comprises, consists essentially of or consists of at least about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, or more consecutive nucleotides. In some embodiments, the nucleic acid fragment comprises, consists essentially of or consists of less than about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450 or 500 consecutive nucleotides.

As used herein with respect to polypeptides, the term "fragment" refers to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, or more consecutive amino acids. In some embodiments, the polypeptide fragment comprises, consists essentially of or consists of less than about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450 or 500 consecutive amino acids.

As used herein with respect to nucleic acids, the term "functional fragment" or "active fragment" refers to nucleic acid that encodes a functional fragment of a polypeptide.

As used herein with respect to polypeptides, the term "functional fragment" or "active fragment" refers to polypeptide fragment that retains at least about 20%, 25%, 30%, 35%, 40%, 45%, 50%, 55%, 60%, 65%, 70%, 75%, 80%, 85%, 90%, 95%, 96%, 97%, 98%, 99%, 99.5% or more of at least one biological activity of the full-length polypeptide (e.g., the ability to up- or down-regulate gene expression). In some embodiments, the functional fragment actually has a higher level of at least one biological activity of the full-length polypeptide.

As used herein, the term "modified," as applied to a polynucleotide or polypeptide sequence, refers to a sequence that differs from a wild-type sequence due to one or more deletions, additions, substitutions, or any combination thereof.

The terms "enhance" and "increase" refer to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The terms "inhibit" and "reduce" or grammatical variations thereof as used herein refer to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable entity or activity (at most, an insignificant amount, e.g., less than about 10% or even 5%).

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts may be referred to as "transcription products" and encoded polypeptides may be referred to as "translation products." Transcripts and encoded polypeptides may be collectively referred to as "gene products." If the polynucleotide is derived from genomic DNA, expression may include splicing of the mRNA in a eukaryotic cell. The expression product itself, e.g., the resulting nucleic acid or protein, may also be said to be "expressed." An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

As used herein, the term "synthetic gene" refers to a nucleic acid sequence generated non-naturally by deliberate human design, the synthetic gene comprising, among other components, a coding region for a protein or nucleic acid of interest, and regulatory regions for expression of the coding region. Structural and functional components of the synthetic gene may be incorporated from differing and/or a plurality of source material. The synthetic gene may be delivered exogenously to a subject, wherein it would be exogenous in comparison to a corresponding endogenous gene. When expressed in a cell, the synthetic gene product may be referred to as a synthetic product (e.g., "synthetic RNA" or "synthetic polypeptide"). Under certain conditions, the synthetic gene may also be interchangeably referred to as a "transgene."

As used herein, the terms "transgenic" and/or "transgene" refer to a nucleic acid sequence containing a functional coding region for a gene that comprises one or more exogenous nucleic acids. The exogenous nucleic acid can be stably integrated within the genome such that the polynucleotide is passed on in successive cell divisions. The exogenous nucleic acid can be integrated into the genome alone or as part of a recombinant expression cassette. "Transgenic" may be used to designate any substrate the genotype of which has been altered by the presence of an exogenous nucleic acid.

The terms "polypeptide," "peptide" and "protein" may be used interchangeably to refer to polymers of amino acids of any length. The terms "nucleic acid," "nucleic acid sequence," and "polynucleotide" may be used interchangeably to refer to polymers of nucleotides of any length. As used herein, the terms "nucleotide sequence," "polynucleotide," "nucleic acid sequence," "nucleic acid molecule" and "nucleic acid fragment" refer to a polymer of RNA, DNA, or RNA and DNA that is single- or double-stranded, optionally containing synthetic, non-natural and/or altered nucleotide bases.

As used herein, the terms "gene of interest," "nucleic acid of interest" and/or "protein of interest" refer to that gene/nucleic acid/protein desired under specific contextual conditions.

The term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. The region in a nucleic acid sequence or polynucleotide in which one or more regulatory elements are found is referred to as a "regulatory region."

The term "coding region" as used herein, refers to the portion of a polynucleotide, e.g., a gene, that encodes a polypeptide.

As used herein with respect to nucleic acids, the term "operably linked" refers to a functional linkage between two or more nucleic acids. For example, a promoter sequence may be described as being "operably linked" to a heterologous nucleic acid sequence because the promoter sequences initiates and/or mediates transcription of the heterologous nucleic acid sequence. In some embodiments, the operably linked nucleic acid sequences are contiguous and/or are in the same reading frame.

A "vector" refers to a compound used as a vehicle to carry foreign genetic material into another cell, where it can be replicated and/or expressed. A cloning vector containing foreign nucleic acid is termed a recombinant vector. Examples of nucleic acid vectors are plasmids, viral vectors, cosmids, expression cassettes, and artificial chromosomes. Recombinant vectors typically contain an origin of replication, a multicloning site, and a selectable marker. The nucleic acid sequence typically consists of an insert (recombinant nucleic acid or transgene) and a larger sequence that serves as the "backbone" of the vector. The purpose of a vector which transfers genetic information to another cell is typically to isolate, multiply, or express the insert in the target cell. Expression vectors (expression constructs or expression cassettes) are for the expression of the exogenous gene in the target cell, and generally have a promoter sequence that drives expression of the exogenous gene. Insertion of a vector into the target cell is referred to transformation or transfection for bacterial and eukaryotic cells, although insertion of a viral vector is often called transduction. The term "vector" may also be used in general to describe items to that serve to carry foreign genetic material into another cell, such as, but not limited to, a transformed cell or a nanoparticle.

By "pharmaceutically acceptable" it is meant a material that is not toxic or otherwise undesirable, i.e., the material may be administered to a subject without causing any undesirable biological effects.

By the terms "treat," "treating," and "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition.

As used herein, the terms "prevent," "prevents," and "prevention" (and grammatical equivalents thereof) refer to a delay in the onset of a disease or disorder or the lessening of symptoms upon onset of the disease or disorder. The terms are not meant to imply complete abolition of disease and encompass any type of prophylactic treatment that reduces the incidence of the condition or delays the onset and/or progression of the condition.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "administering" and "administration" of a synthetic gene, expression cassette, vector, plasmid, viral vector, transformed cell, nanoparticle (including all extracellular vesicles), or pharmaceutical composition to a subject include any route of introducing or delivering to a subject a compound to perform its intended function. Administration can be carried out by any suitable route, including orally, intranasally, parenterally (intravenously, intramuscularly, intraperitoneally, intracisternally, intrathecally, intraventricularly, or subcutaneously), or topically. Administration includes self-administration and administration by another.

As used herein, the term "extracellular vesicles" refers to lipid-bound particles that are released from cells. The term encompasses, without limitation, exosomes, ectosomes, microvesicles, microparticles, nanoparticles, large EVs, and autophagosomes, and range in diameter from 20-30 nm to 10 microns or more. Extracellular vesicles carry a cargo of proteins, nucleic acids, lipids, metabolites, and/or organelles from the parent cell.

As used herein, the term "muscle-related disorder, condition, or damage" refers to a disorder, condition, or damage that occurs in muscle cells or tissue and may include skeletal muscle, cardiac muscle, and/or smooth muscle. The disorder, condition, or damage may be due to an issue (e.g., mutation or trauma) that originates in muscle cells or tissue or to an issue that originates outside of muscle cells or tissue but results in a disorder, condition, or damage in muscle.

As used herein, the term "neurological disorder, condition, or damage" refers to a disorder, condition, or damage that occurs in neurological cells or tissue, e.g., in the central nervous system and/or peripheral nervous system, e.g., in neurons, oligodendrocytes, glial cells, astrocytes, and/or Schwann cells. The disorder, condition, or damage may be due to an issue (e.g., mutation or trauma) that originates in neurological cells or tissue or to an issue that originates outside of neurological cells or tissue but results in a disorder, condition, or damage in the nervous system.

As used herein, the term "neuromuscular disorder, condition, or damage" refers to a disorder, condition, or damage that occurs in muscle cells or tissue or in neurological cells or tissue, e.g., in the central nervous system and/or peripheral nervous system. The disorder, condition, or damage may be due to an issue (e.g., mutation or trauma) that originates in muscle or neurological cells or tissue or to an issue that originates outside of muscle or neurological cells or tissue but results in a disorder, condition, or damage in muscle or the nervous system.

Methods of Isolating Extracellular Vesicles

A first aspect of the invention relates to methods of isolating muscle-derived EVs from bodily fluids and isolating EVs from cultured cells. Thus, one aspect of the invention relates to a method of isolating muscle-derived extracellular vesicles from a bodily fluid, comprising: a) contacting the bodily fluid with a capture agent that specifically binds to a molecule on the surface of muscle-derived extracellular vesicles to form a capture agent:extracellular vesicle complex; and b) isolating the capture agent:extracellular vesicle complex from the bodily fluid. Muscle-derived EVs are defined as EVs that are released from muscle cells. The muscle cells may be skeletal muscle, cardiac muscle, smooth muscle, or any combination thereof.

EVs may be isolated from any bodily fluid, including without limitation, blood, serum, plasma, urine, saliva, sputum, CSF, sweat, milk, ascites, cyst fluid, pleural fluid, peritoneal fluid, intestinal fluid, fecal fluid, or tears. For blood, it is preferable to isolate the EVs from plasma or serum. In some embodiments, the plasma or serum is diluted about 1-3 fold with an isotonic solution, e.g., phosphate buffered saline, prior to isolation of the EVs.

The capture agent may be conjugated to a solid support to aid in the isolation process. The solid support may be, for example, a bead, e.g., a magnetic bead. After contacting the bodily fluid and binding to a molecule on the EVs, the conjugated capture agent may be isolated by techniques such as centrifugation and magnetic separation.

The capture agent may be any molecule that can specifically bind a target molecule. In some embodiments, the muscle-derived EVs may be identified and/or isolated based on a unique combination of target molecules. Examples of capture agents include, without limitation, an antibody, antibody fragment, antibody derivative, oligonucleotide, aptamer, or aptamer-based biosensor (e.g., aptosensor). Any of the capture agents may be conjugated to a binding agent, e.g., an antibody, e.g., that binds directly or indirectly to a solid support. For example, an antibody that binds a molecule on the EVs may be bound by protein A containing avidin or streptavidin and the solid support may be coating with biotin. As another example, the capture agent may be an oligonucleotide conjugated to an antibody and the solid support may be coated with protein A to bind the antibody.

In some embodiments, the capture agent may be an agent that generally binds lipids and can be used to bind and isolate all EVs. An example is an isolation reagent comprising F68, e.g., an isolation reagent comprising F68, phosphate buffered saline, BSA, and protease and phosphatase inhibitors. In some embodiments, the isolation reagent may comprise a capture agent as described above.

The capture agent may specifically bind any molecule that uniquely identifies the EVs as muscle-derived. Exemplary target molecules include, without limitation, the proteins listed in Table 1. Table 1 includes an NCBI accession number of an exemplary protein sequence and the name of the gene encoding the protein.

TABLE 1

| Protein | Accession No. | Gene |
|---|---|---|
| Cardiac muscle fast twitch 1 calcium-transporting ATPase | AAB53113 | ATP2A1 |
| Voltage-dependent calcium channel gamma subunit 1 | NP_000718 | CACNG1 |
| Ryanodine receptor 1 | P21817 | RYR1 |
| Alpha-sarcoglycan | AAH25702 | SGCA |
| Sodium-potassium transporting ATPase alpha 2 polypeptide | AAH52271 | ATP1A2 |
| Beta-1-syntrophin | NP_066301 | SNTB1 |
| Beta-sarcoglycan | CAG33091 | SGCB |
| Myoferlin | AAF27177 | MYOF |
| Transmembrane protein 8C | NP_001073952 XP_372180 | TMEM8C |
| Junctional sarcoplasmic reticulum protein 1 | EAW69396 | JSRP1 |
| Tripartite motif containing 72 | AAH33211 | TRIM72 |
| Adenylosuccinate synthase like 1 | EAW81876.1 | ADSSL1 |
| Cardiac muscle beta myosin heavy chain 7B | AAH69327.2 | MYH7B |
| SH3 and cysteine rich domain 3 | AAH08069.1 | STAC3 |
| Kelch-like family member 41 | NP_006054.2 | KLHL41 |
| Obscurin, cytoskeletal calmodulin and titin-interacting RhoGEF | AAI14462.1 | OBSCN |
| Adenylate cyclase-associated protein 2 | AAA20587.1 | CAP2 |
| Protein kinase C and casein kinase substrate in neurons 3 | AAG31023.1 | PACSIN3 |
| Junctophilin 1 | NP_001349980.1 | JPH1 |
| Junctophilin 2 | Q9BR39.2 | JPH2 |
| Reticulon 2 | NP_005610.1 | RTN2 |
| Nicotinic cholinergic receptor alpha 1 | EAX11128.1 | CHRNA1 |
| Phosphatidic acid phosphatase type 2 domain containing 3 | EAW87966.1 | PPAPDC3 |
| Integrin alpha-7 | AAC39708.1 | ITA7 |
| Skeletal muscle alpha actin | CAG38754.1 | ACTS |
| Actinin alpha 3 | EAW74546.1 | |
| Myomaker | NM_001080483.2 | MYMK |
| Myomerger | NP_001302423.1 | |

Another aspect of the invention relates to a method of isolating extracellular vesicles from a cell culture medium, comprising: a) providing cell culture medium in which cells were grown; b) contacting the cell culture medium with a capture agent that specifically binds to a molecule on the surface of the extracellular vesicles to form a capture agent:extracellular vesicle complex; and c) isolating the capture agent:extracellular vesicle complex from the cell culture medium.

In some embodiments, the cells may be, without limitation, muscle satellite cells, primary muscle cells, HEK293 cells, HEK293T cells, CAP cells, mesenchymal stem cells, immune cells, or any combination thereof. In some embodiments, the cells are HEK293 cells or HEK293T cells. Preferably, the cell medium used for the cells is EV-free, e.g., by using serum-free medium or using serum depleted of EVs.

In some embodiments, the EVs may be removed from the capture agent after isolation, e.g., by increasing the salt concentration and/or lowering the pH. In other embodiments, The EVs may be further manipulated (e.g., characterized) while remaining bound to the capture agent.

Diagnostic Methods Using Extracellular Vesicles

Another aspect of the invention relates to diagnostic methods using EVs. These methods are based on the ability to isolate tissue-specific EVs from bodily fluids and characterization of the cargo of the EVs as biomarkers for detecting and monitoring disease and/or damage to tissues (e.g., a "liquid biopsy"). The ability to diagnose and monitor disorders by isolating and characterizing EVs from bodily fluids may avoid or reduce the use of more invasive and painful techniques such as muscle biopsies and allows for more frequent monitoring than would otherwise be tolerated.

Thus, one aspect of the invention relates to a method of detecting a muscle-related disorder, condition, or damage in a subject, comprising: a) isolating muscle-derived extracellular vesicles from a bodily fluid of the subject; b) characterizing one or more components within or on the extracellular vesicles; and c) detecting a muscle-related disorder, condition, or damage based on the characterization of the one or more components or absence of one or more components within or on the extracellular vesicles. In some embodiments, 1, 2, 3, 4, or 5 or more components are characterized.

The one or more components may be any components that are biomarkers of a muscle-related disorder, condition, or damage. In some embodiments, the one or more components are proteins, DNAs, RNAs, and/or organelles. The one or more components may be any of the proteins, DNAs, or RNAs listed in Table 2 or any combination thereof. Characterization of the components may include determining any characteristic of the component that serves as a biomarker providing information regarding the muscle-related disorder, condition, or damage. In some embodiments, characterizing the one or more components within or on the EVs comprises determining the presence, absence, abundance, molecular weight and/or sequence of the one or more components.

Once the EVs are isolated, the components may be obtained by lysing the EVs and collecting the cargo within the EVs and/or collecting the components in or on the lipid membrane for characterization. In some embodiments, the EVs may be lysed while bound to the capture agent.

The bodily fluid may be any bodily fluid in which muscle-derived EVs can be found, including without limitation, blood, serum, plasma, urine, saliva, sputum, CSF, sweat, milk, ascites, cyst fluid, pleural fluid, peritoneal fluid, intestinal fluid, fecal fluid, or tears.

The muscle-derived EVs may be isolated, for example, by the methods disclosed above, e.g., using a capture agent such as the ones disclosed in Table 1.

The muscle-related disorder, condition, or damage may be any disorder, condition, or damage known to be correlated with a biomarker found in muscle-derived EVs. Non-limiting examples of muscle-related disorders, conditions, or damage and the biomarkers associated with them are listed in Table 2. Muscle pathology that can be detected and/or monitored may be secondary to other conditions such as aging, cancer, diabetes, renal failure, disuse, mechanical ventilation, space flight, cast immobilization, spinal cord injury, sepsis, starvation or glucocorticoid treatment. Muscle damage that can be detected and/or monitored may be due to, e.g., crush injury, sports injury, or traumatic damage.

A further aspect of the invention relates to a method of determining a risk of having a muscle-related disorder, condition, or damage in a subject, comprising: a) isolating muscle-derived extracellular vesicles from a bodily fluid of the subject; b) characterizing one or more components within or on the extracellular vesicles; and c) determining a risk of having a muscle-related disorder, condition, or damage based on the characterization of the one or more components or absence of one or more components within or on the extracellular vesicles. In some embodiments, 1, 2, 3, 4, or 5 or more components are characterized.

The method may be used to identify subjects that have a disorder, condition, or damage but do not exhibit symptoms. The method may be used to monitor subjects that are suspected of having a disorder or damage for changes in components that are indicative of possible, impending or worsening conditions or damage. This method may also identify non-manifesting carriers of a disorder.

The one or more components may be any components that are biomarkers of a muscle-related disorder, condition, or damage. In some embodiments, the one or more components are proteins, DNAs, RNAs, and/or organelles (e.g., mitochondria). The one or more components may be any of the proteins, DNAs, or RNAs listed in Table 2 or any combination thereof. Characterization of the components may include determining any characteristic of the component that serves as a biomarker providing information regarding the muscle-related disorder, condition, or damage. In some embodiments, characterizing the one or more components within or on the EVs comprises determining the presence, absence, abundance, molecular weight and/or sequence of the one or more components.

The bodily fluid may be any bodily fluid in which muscle-derived EVs can be found, including without limitation, blood, serum, plasma, urine, saliva, sputum, CSF, sweat, milk, ascites, cyst fluid, pleural fluid, peritoneal fluid, intestinal fluid, fecal fluid, or tears.

The muscle-derived EVs may be isolated, for example, by the methods disclosed above, e.g., using a capture agent such as the ones disclosed in Table 1.

The muscle-related disorder, condition, or damage may be any disorder, condition, or damage known to be correlated with a biomarker found in muscle-derived EVs. Non-limiting examples of muscle-related disorders, conditions, or damage and the biomarkers associated with them are listed in Table 2.

TABLE 2

| Disease | Genetic Mutation | Protein | Exemplary Accession No. |
|---|---|---|---|
| Congenital Muscular Dystrophies | | | |
| CMD with cardiomyopathy | Titin | Titin | CAA62188 |
| CMD with desmin inclusions (abnormal accumulations of the muscle protein desmin in some muscle fibers) | SEPN1 or Selenon | selenoprotein N | NP_996809 |
| CMD with integrin alpha 7 mutations | integrin-alpha 7 | integrin-alpha 7 | AAC18968 |
| CMD with joint hyperlaxity | integrin alpha 9 | integrin alpha 9 | EAW64501 |
| CMD with familial junctional epidermolysis bullosa | plectin protein | plectin protein | CAA91196 |
| CMD with muscle hypertrophy | fukutin-related protein (FKRP) | fukutin-related protein (FKRP) | AAH02612 |
| MDC1C | fukutin-related protein (FKRP) | fukutin-related protein (FKRP) | AAH02612 |
| MDC1D | LARGE gene | LARGE xylosyl- and glucuronyltransferase 1 | CAG30396 |
| CMD with myasthenic syndrome | DOK7 gene | docking protein 7 | NP_001288000 XP_005248013 |
| CMD with (early) spinal rigidity | SEPN1 or Selenon | selenoprotein N | NP_996809 |
| CMD with spinal rigidity and lamin A/C abnormality | lamin A or C proteins | lamin A or C proteins | NP_001269554, NP_733821 |
| CMD with spinal rigidity and selenoprotein deficiency | SBP2 gene | SECIS binding protein 2 | AAH01189 |
| CMD with structural abnormalities of mitochondria (energy-producing subunits of cells) | choline kinase beta gene | choline kinase beta | AAI01489 |
| MDDGA4 | fukutin gene | fukutin | BAA94082 |
| MDC1A | laminin alpha 2 gene | laminin alpha 2 | EAW48082 |
| Santavuori muscle-eye-brain disease | POMGnT1 gene | protein O-linked mannose N-acetylglucosaminyltransferase 1 (beta 1,2-) | NP_001230695 |
| Ullrich CMD | COLGA1, COL6A2 or COL6A3 genes | collagen type VI alpha 1 chain, 2 chain, and 3 chain | AAH52575, AAH02484, AAI50626 |
| MDDGA type | B3GNT1 gene | UDP-GlcNAc: betaGal beta-1,3-N-acetylglucosaminyltransferase 2 | |
| MDDGA1 type | POMT1 gene | protein O-mannosyltransferase 1 | BAX07485 |
| MDDGA2 type | POMT2 gene | protein O-mannosyltransferase 2 | AAF62558 |
| MDDGA8 type | GTDC2 gene | protein O-linked mannose N-acetylglucosaminyltransferase 2 (beta 1,4-) | NP_116195 |

TABLE 2-continued

| Disease | Genetic Mutation | Protein | Exemplary Accession No. |
|---|---|---|---|
| MDDGA10 type | TMEM5 gene | ribitol xylosyltransferase 1 | AAH02596 |
| MDDGA11 type | B3GALNT2 gene | beta-1,3-N-acetylgalactosaminyltransferase 2 | AAH16974 |
| MDDGA12 type | SGK196 gene | protein O-mannose kinase | AAI13704 |
| Other | | | |
| Duchenne muscular dystrophy | Dystrophin | Dystrophin | AAA53189 |
| Becker muscular dystrophy | Dystrophin | Dystrophin | AAA53189 |
| Carriers of Duchenne or Becker MD | Dystrophin | Dystrophin | AAA53189 |
| Emery-Dreifuss Muscular Dystrophy | emerin, lamin A, lamin C | emerin, lamin A, lamin C | NP_000108, NP_001269554, NP_733821 |
| Facioscapulohumeral Muscular Dystrophy (FSH, FSHD) | Unknown; short DNA segment on Chromosome 4 | | |
| Myotonic Dystrophy (DM) 1 | DMPK contains an abnormally expanded section | DM1 protein kinase | AAH26328 |
| Myotonic Dystrophy (DM) 2 | ZNF9 | CCHC-type zinc finger nucleic acid binding protein | AAR89462 AAK91676 |
| Oculopharyngeal Muscular Dystrophy (OPMD) | PABPN1 | poly(A) binding protein nuclear 1 | AAH10939 |
| Friedreich's Ataxia (FA) | frataxin | frataxin | AAA98509 |
| Mitochondrial Myopathies | genes involved in mitochondrial disease normally make proteins that work inside the mitochondria | | |
| Mitochondrial Myopathies | mitochondria are often damaged as a result of aging | | |
| Mitochondrial Myopathies | mitochondria are often damaged as a result of cancer treatments | | AAA53189 |
| Dominant Limb Girdle Muscular Dystrophy Subtype Numbers | | | |
| LGMD1A | MYOT mutation | myotilin | AAD44754 |
| LGMD1B | LMNA mutation | lamin A/C | NP_001269554, NP_733821 |
| LGMD1C | CAV3 mutation | caveolin 3 | CAA75042 |
| LGMD1D | DNAJB6 mutation | DnaJ heat shock protein family (Hsp40) member B6 | CAG38529 |
| LGMD1E | DES mutation | desmin | NP_001918 |
| LGMD1F | TNP03 mutation | transportin 3 | EAL24106 |
| Recessive Limb Girdle Muscular Dystrophy Subtype Numbers | | | |
| LGMD2A | CAPN3 mutations | calpain 3 | AAD28253 |
| LGMD2B | DYSF mutations | dysferlin | AAC63519 |
| LGMD2C, also called SCARMD1 | SGCG mutations | sarcoglycan gamma | NP_000222 |
| LGMD2D, also called SCARMD2 | SGCA mutations | sarcoglycan alpha | AAH25702 |
| LGMD2E | SGCB mutations | sarcoglycan beta | CAG33091 |
| LGMD2F | SGCD mutations | sarcoglycan delta | AAH20740 |
| LGMD2G | TCAP mutations | titin-cap | NP_003664 |
| LGMD2H | TRIM32 mutations | tripartite motif containing 32 | NP_036342 |
| LGMD2I | FKRP mutations | fukutin related protein | NP_001034974 |
| LGMD2J | TTN mutations | titin | CAA62188 |
| LGMD2K | POMT1 mutations | protein O-mannosyltransferase 1 | BAX07485 |
| LGMD2L | ANO5 mutations | anoctamin 5 | NP_998764 |
| LGMD2M | FKTN mutations | fukutin | AAI17701 |
| LGMD2N | POMT2 mutations | protein O-mannosyltransferase 2 | AAF62558 |
| LGMD2O | POMGnT1 mutations | protein O-linked mannose N-acetylglucosaminyltransferase 1 (beta 1,2-) | NP_001230695 |
| LGMD2P | DAG1 mutations | dystroglycan 1 | NP_004384 |
| LGMD2Q | PLEC1 mutations | plectin | CAA91196 |
| LGMD2R | DES mutations | desmin | NP_001918 |
| LGMD2S | TRAPPC11 mutations | trafficking protein particle complex 11 | NP_068761 |
| LGMD2T | GMPPB mutations | GDP-mannose pyrophosphorylase B | NP_068806 |
| LGMD2U | ISPD mutations | CDP-L-ribitol pyrophosphorylase A | NP_001094896 XP_001126777 XP_001131763 XP_001132057 |
| LGMD2V | GAA mutations | glucosidase alpha, acid | XP_005257251 |
| LGMD2W | LIMS2 mutations | LIM zinc finger domain containing 2 | AAM77350 |
| LGMD2X | BVES mutations | blood vessel epicardial substance | AAH40502 |
| LGMD2Y | TOR1AIP1 mutations | torsin 1A interacting protein 1 | NP_001254507 |

TABLE 2-continued

| Disease | Genetic Mutation | Protein | Exemplary Accession No. |
|---|---|---|---|
| Congenital Myopathies | | | |
| Centronuclear myopathies, including myotubular myopathy | deficiencies of myotubularin | myotubularin | NP_000243 |
| Central core disease/malignant hyperthermia susceptibility | Defects of ryanodine receptor and/or Ca handling protein | Ryanodine receptor or Ca handling protein | P21817 |
| Centronuclear myopathies, including myotubular myopathy | defects or deficiencies of myotubularin | myotubularin | NP_000243 |
| Nemaline myopathy (rod body disease) | | | |
| Distal Muscular Dystrophies | | | |
| Finnish (tibial) distal myopathy | Titin | Titin | CAA62188 |
| Gowers-Laing distal myopathy | mutations in the MYH7 gene, which instructs for myosin heavy chain 7, a protein that participates in muscle contraction | myosin heavy chain 7 | NP_000248 XP_005267753 |
| Hereditary inclusion-body myositis (myopathy) type 1 (HIBM1) | abnormal clumps of cellular material; and vacuoles, which are cellular bubbles. The cause is unknown. | | |
| Miyoshi distal myopathy | Dysferlin | Dysferlin | AAC63519 |
| Nonaka distal myopathy (inclusion body myopathy) | GNE gene | glucosamine (UDP-N-acetyl)-2-epimerase/N-acetylmannosamine kinase | NP_001121699 |
| VCP Myopathy/IBMPFD | VCP or p97 | valosin containing protein | AAI22551 |
| Metabolic Myopathies | | | |
| Acid maltase deficiency (Type II GSD; Pompe disease) | Acid alpha-glucosidase | Acid alpha-glucosidase | AAA52506 |
| Carnitine deficiency | Primary - missing carnitine transporter; secondary - happens in other metabolic diseases | | |
| Carnitine palmityl transferase deficiency | carnitine palmityl transferase 2 enzyme (CPT2) | carnitine palmityl transferase 2 enzyme | EAX06753 |
| Debrancher enzyme deficiency (GDS Type III; Cori or Forbes disease) | defect in the debrancher enzyme gene, which interferes with the breakdown of glycogen | debrancher enzyme | NP_000633 |
| Lactate dehydrogenase deficiency | lactate dehydrogenase enzyme | lactate dehydrogenase enzyme | CAE11711 |
| Myoadenylate deaminase deficiency | Myoadenylate deaminase deficiency | Myoadenylate deaminase | NP_000027 |
| Phosphofructokinase deficiency (GSD VII; Tarui disease) | Phosphofructokinase deficiency | Phosphofructokinase | AAA91985 |
| Phosphoglycerate kinase deficiency | phosphoglycerate kinase enzyme | phosphoglycerate kinase enzyme | AAA60078 |
| Phosphoglycerate mutase deficiency | phosphoglycerate mutase enzyme | phosphoglycerate mutase enzyme | AAA64238 |
| Phosphorylase deficiency (GDS Type V; McArdle disease) | phosphorylase (also known as myophosphorylase) enzyme | phosphorylase (also known as myophosphorylase) enzyme | NP_005600 |
| Type IV - Anderson's Disease | Glycogen branching enzyme | Glycogen branching enzyme | NP_000149 |
| GSD X/GSD 10 | Phosphoglycerate mutase | Phosphoglycerate mutase | AAA64238 |
| GSD XII/GSD 12 | Aldolase A | Aldolase A | CAA30979 |
| GSD XIII/GSD 13 | β-enolase | β-enolase | NP_443739 |
| GSD XV/GSD 15 | Glycogenin-1 | Glycogenin-1 | AAD31084 |
| Others | | | |
| myoclonic epilepsy | CSTB, EPM2A, NHLRC1, mitochondrial disorders | cystatin B; EPM2A glucan phosphatase, laforin; NHL repeat containing E3 ubiquitin protein ligase 1 | NP_000091.1, AAH05286.1, NP_940988.2, mito replacement |
| autosomal dominant adult-onset leukodystrophy | CSF1R | colony stimulating factor 1 receptor | AAH47521.1 |
| epsilon sarcoglycanopathy | SGCE | sarcoglycan epsilon | AAQ89401.1 |
| Compton-North congenital myopathy | CNTN1 | contactin 1 | AAH36569 |
| early onset myopathy, areflexia, respiratory distress, and dysphagia | MEGF10 | multiple EGF like domains 10 | AAH20198.1 |
| hypertrophic cardiomyopathy 4 | MYBPC3 | myosin binding protein C, cardiac | ABQ59032.1 |
| proximal myopathy and ophthalmoplegia | MYH2 | myosin heavy chain 2 | AAH93082.1 |
| myotubular myopathy | MTM1 | myotubularin 1 | NP_000243.1 |
| Leukodystrophy, adult-onset, autosomal dominant | LMNB1 | Lamin B1 | NP_005564.1 |
| Neurofibromatosis Type 1 | NF1 | neurofibromin | BAA02150.1 |
| Methylmalonic acidemia | MUT | methylmalonyl-CoA mutase | ALQ33660.1 |
| Methylmalonic acidemia, Homocysteinuria | MMACHC | Cobalamin C | AAH06122.3 |
| Epilepsy, progressive myoclonic, 9 | LMNB2 | Lamin B2 | NP_116126.3 |
| Friedreich's Ataxia | FXN | Frataxin | AAH23633.1 |
| Meconium ileus in cystic fibrosis | CFM1 | Cystic Fibrosis Modifier 1 | |

TABLE 2-continued

| Disease | Genetic Mutation | Protein | Exemplary Accession No. |
|---|---|---|---|
| Tay-Sachs | HEXA | β-Hexosaminidase A | AAB00965.1 |
| Left ventricular noncompaction | DTNA | Dystrobrevin alpha | AAH05300.1 |
| Left ventricular noncompaction | DTNB | Dystrobrevin beta | XP_024308511.1 |
| Epidermolysis bullosa, Neuropathy, hereditary sensory and autonomic, type VI | DST | Dystonin | AAH65536.1 |
| Nemaline Myopathies | | | |
| | NEB | Nebulin | NP_001157979.1 |
| | ACTA1 | actin alpha 1, skeletal muscle | CAG38754.1 |
| | TPM3 | Tropomyosin 3 | AAH62740.1 |
| | TPM2 | Tropomyosin 2 | EAW58358.1 |
| | TNNT1 | Troponin TI, slow skeletal muscle | AAI07799.1 |
| | CFL2 | Cofilin 2 | AAF97934.1 |
| | KBTBD13 | kelch repeat and BTB domain containing 13 | NP_001094832.1 |
| | KLHL40 | kelch like family member 40 | NP_689606.2 |
| | KLHL41 | kelch like family member 41 | NP_006054.2 |
| | LMOD3 | leiomodin 3 | AAH39202.1 |
| Centronuclear myopathies | | | |
| | MTM1 | myotubularin 1 | NP_000243.1 |
| | BINI | bridging integrator 1 | NP_647601.1 |
| | RYR1 | ryanodine receptor 1 | P21817.3 |
| | TTN | titin | XP_016860308.1 |
| | DNM2 | dynamin 2 | AAH39596.1 |
| | MYF6 | myogenic factor 6 | CAG46563.1 |
| | MTMR14 | myotubularin related protein 14 | NP_001070993.1 |
| Hypertrophic cardiomyopathy | | | |
| | MYH7 | myosin heavy chain 7 | NP_000248.2 |
| | MYBPC3 | myosin binding protein C, cardiac | ABQ59032.1 |
| | TNNT2 | troponin T2, cardiac type | AAK92231.1 |
| | TNNI3 | troponin I3, cardiac type | CAG46782.1 |
| Malignant hyperthermia susceptibility | | | |
| Type 1 | RYR1 | ryanodine receptor 1 | P21817.3 |
| Type 5 | CACNA1S | calcium voltage-gated channel subunit alpha1 S | AAI33672.1 |
| Type 2 | unknown | | |
| Type 3 | CA2D1 | voltage-dependent calcium channel subunit alpha-2/delta-1 precursor | P54289 |
| Type 4 | unknown | | |
| Type 6 | unknown | | |
| Dilated cardiomyopathy | | | |
| | LDB3 | LIM domain binding 3 | ALQ34003.1 |
| | MYOZ2 | myozenin 2 | NP_057683.1 |
| | CALR3 | calreticulin 3 | EAW84546.1 |
| | TBX20 | T-box transcription factor 20 | NP_001071121.1 |
| | COA6 | cytochrome c oxidase assembly factor 6 | NP_001193570.2 |
| | MYL3 | myosin light chain 3 | NP_000249.1 |
| | MYL2 | myosin light chain 2 | CAG33243.1 |
| | LAMP2 | lysosomal associated membrane protein 2 | AAB67314.1 |
| | FKTN | fukutin | AAI17701.1 |
| | MT-TL1 | mitochondrially encoded tRNA leucine 1 | |
| | MYH6 | myosin heavy chain 6 | NP_002462.2 |
| | DSP | desmoplakin | NP_001305963.1 |
| | DNAJC19 | DnaJ heat shock protein family (Hsp40) member C19 | NP_660304.1 |
| | DOLK | dolichol kinase | NP_055723.1 |
| | ABCC9 | ATP binding cassette subfamily C member 9 | AAH33804.1 |
| | EYA4 | EYA transcriptional coactivator and phosphatase 4 | CAA76636.1 |
| | PDCD1 | programmed cell death 1 | AAO63583.1 |
| | PLN | phospholamban | NP_002658.1 |
| | TAZ | tafazzin | NP_000107.1 |
| | NEXN | nexilin F-actin binding protein | AAI11396.1 |
| | GATAD1 | GATA zinc finger domain containing 1 | AAH31091.1 |
| | CSRP3 | cysteine and glycine rich protein 3 | AAH24010.1 |
| | RBM20 | RNA binding motif protein 20 | NP_001127835.2 |
| | VCL | vinculin | NP_003364.1 |

TABLE 2-continued

| Disease | Genetic Mutation | Protein | Exemplary Accession No. |
|---|---|---|---|
| | HSD17B10 | hydroxysteroid 17-beta dehydrogenase 10 | ALQ33565.1 |
| | JUP | junction plakoglobin | AAH11865.1 |
| | MT-TV | mitochondrially encoded tRNA valine | |
| | RAF1 | Raf-1 proto-oncogene, serine/threonine kinase | NP_001341618.1 |
| | ACE | angiotensin I converting enzyme | EAW94319.1 |
| | IDH2 | isocitrate dehydrogenase (NADP(+)) 2, mitochondrial | NP_002159.2 |
| | MT-TK | mitochondrially encoded tRNA lysine | |
| | RYR2 | ryanodine receptor 2 | NP_001026.2 |
| | GLB1 | galactosidase beta 1 | AAH07493.1 |
| | MLYCD | malonyl-CoA decarboxylase | AAH00286.1 |
| | APOA1 | apolipoprotein A1 | AAS68227.1 |
| | TMEM70 | transmembrane protein 70 | EAW87022.1 |
| | SMAD4 | SMAD family member 4 | AAH02379.1 |
| | CAV3 | caveolin 3 | NP_203123.1 |
| | PRKAG2 | protein kinase AMP-activated non-catalytic subunit gamma 2 | NP_057287.2 |
| | PKP2 | plakophilin 2 | ACD13293.1 |
| | CPS1 | carbamoyl-phosphate synthase 1 | CAA75785.1 |
| | MYH7 | myosin heavy chain 7 | NP_000248.2 |
| | TPM1 | tropomyosin 1 | NP_001018005.1 |
| | MT-TH | mitochondrially encoded tRNA histidine | |
| | DSC2 | desmocollin 2 | AAH63291.1 |
| | NDUFB9 | NADH: ubiquinone oxidoreductase subunit B9 | NP_004996.1 |
| | NDUFV2 | NADH: ubiquinone oxidoreductase core subunit V2 | AAH17487.1 |
| | TMEM43 | transmembrane protein 43 | NP_077310.1 |
| | SOD2 | superoxide dismutase 2 | NP_001309743.1 |
| | MYBPC3 | myosin binding protein C, cardiac | NP_000247.2 |
| | SLC25A4 | solute carrier family 25 member 4 | AAH61589.1 |

An additional aspect of the invention relates to a method of monitoring progression of a muscle-related disorder, condition, or damage in a subject, comprising: a) isolating muscle-derived extracellular vesicles from a bodily fluid of the subject at two or more time points; b) characterizing one or more components within or on the extracellular vesicles at each time point; and c) monitoring progression of a muscle-related disorder, condition, or damage based on changes in the characteristics of the one or more components or absence of one or more components within or on the extracellular vesicles at each time point. In some embodiments, 1, 2, 3, 4, or 5 or more components are characterized.

The method may be used to monitor subjects that have been diagnosed with a disorder, condition, or damage but do not exhibit symptoms or exhibit mild symptoms to determine if the disease, condition, or damage is worsening or improving over time. EVs may be isolated from the subject at regular intervals, e.g., every day, every week, every 1, 3, 6, or 12 months, or any other suitable interval. The same components or additional components may be characterized in each sample to monitor changes in the components, e.g., increasing or decreasing amounts, appearance or disappearance of variants or mutants, etc.

The one or more components may be any components that are biomarkers of a muscle-related disorder, condition, or damage. In some embodiments, the one or more components are proteins, DNAs, RNAs, and/or organelles. The one or more components may be any of the proteins, DNAs, or RNAs listed in Table 2 or any combination thereof. Characterization of the components may include determining any characteristic of the component that serves as a biomarker providing information regarding the muscle-related disorder, condition, or damage. In some embodiments, characterizing the one or more components within or on the EVs comprises determining the presence, absence, abundance molecular weight and/or sequence of the one or more components.

The bodily fluid may be any bodily fluid in which muscle-derived EVs can be found, including without limitation, blood, serum, plasma, urine, saliva, sputum, CSF, sweat, milk, ascites, cyst fluid, pleural fluid, peritoneal fluid, intestinal fluid, fecal fluid, or tears.

The muscle-derived EVs may be isolated, for example, by the methods disclosed above, e.g., using a capture agent such as the ones disclosed in Table 1.

The muscle-related disorder, condition, or damage may be any disorder, condition, or damage known to be or later discovered to be correlated with a biomarker found in muscle-derived EVs. The biomarker may be one that is directly related to the cause of the disorder, condition, or damage (e.g., a mutated gene) or one that indirectly related to the disorder, condition, or damage (e.g., as a consequence of the mutated gene). Non-limiting examples of muscle-related disorders, conditions, or damage and the proteins and nucleic acids associated with them are listed in Table 2.

Another aspect of the invention relates to a method of monitoring effectiveness of a treatment of a muscle-related disorder, condition, or damage in a subject, comprising: a) isolating muscle-derived extracellular vesicles from a bodily fluid of the subject at two or more time points before and/or during treatment; b) characterizing one or more components within or on the extracellular vesicles at each time point; and c) monitoring effectiveness of the treatment of a muscle-related disorder, condition, or damage based on changes in the characteristics of the one or more components or absence of one or more components within or on the extracellular vesicles at each time point. In some embodiments, 1, 2, 3, 4, or 5 or more components are characterized.

EVs may be isolated from the subject at regular intervals, e.g., every day, every week, every 1, 3, 6, or 12 months, or any other suitable interval. The first samples(s) may be taken prior to the start of the treatment and may continue throughout the treatment and beyond the end of the treatment. The same components or additional/alternative components may be characterized in each sample to monitor changes in the components, e.g., increasing or decreasing amounts, appearance or disappearance of variants or mutants, etc. For example, when a subject is being treated with a replacement protein, e.g., dystrophin, the isolated EVs may be characterized for the appearance and/or abundance of the replacement protein as an indication of the effectiveness of the treatment. Similarly, when a subject is being treated with gene therapy to provide a replacement protein, the isolated EVs may be characterized for the appearance and/or abundance of the replacement protein or the nucleic acid encoding the replacement protein as an indication of the effectiveness of the treatment.

The one or more components may be any components that are biomarkers of a muscle-related disorder, condition, or damage. In some embodiments, the one or more components are proteins, DNAs, RNAs, and/or organelles. The one or more components may be any of the proteins, DNAs, or RNAs listed in Table 2 or any combination thereof. Characterization of the components may include determining any characteristic of the component that serves as a biomarker providing information regarding the muscle-related disorder, condition, or damage. In some embodiments, characterizing the one or more components within or on the EVs comprises determining the presence, absence, abundance, molecular weight and/or sequence of the one or more components.

The bodily fluid may be any bodily fluid in which muscle-derived EVs can be found, including without limitation, blood, serum, plasma, urine, saliva, sputum, CSF, sweat, milk, ascites, cyst fluid, pleural fluid, peritoneal fluid, intestinal fluid, fecal fluid, or tears.

The muscle-derived EVs may be isolated, for example, by the methods disclosed above, e.g., using a capture agent such as the ones disclosed in Table 1.

The muscle-related disorder, condition, or damage may be any disorder, condition, or damage known to be correlated with a biomarker found in muscle-derived EVs. Non-limiting examples of muscle-related disorders, conditions, or damage and the biomarkers associated with them are listed in Table 2.

Screening Methods Using Extracellular Vesicles

A further aspect of the invention relates to the use of the isolated EVs of the present invention as the basis for screening methods for effective treatments and therapeutic agents for disorders, conditions, or damage. The isolation of EVs and characterization of components provides an efficient and convenient method for monitoring changes in cells and animals as result of exposure to treatments and agents.

Thus, one aspect of the invention relates to a method of identifying an effective therapy for a muscle-related disorder, condition, or damage, comprising: a) providing a candidate therapy to a subject or an in vivo or in vitro model of a muscle-related disorder, condition, or damage; b) isolating muscle-derived extracellular vesicles from cells or tissues of the subject or in vivo or in vitro model at two or more time points before, during, and/or after the candidate therapy and/or comparing a single time point from treated and untreated model experimental units/groups; c) characterizing one or more components within or on the extracellular vesicles at each time point; and d) identifying an effective therapy for the muscle-related disorder, condition, or damage based on changes in the characteristics of the one or more components or absence of one or more components within or on the extracellular vesicles at each time point. In some embodiments, 1, 2, 3, 4, or 5 or more components are characterized.

Another aspect of the invention relates to a method of identifying an effective therapeutic agent for a muscle-related disorder, condition, or damage; comprising: a) providing a candidate therapeutic agent to a subject or an in vivo or in vitro model of a muscle-related disorder, condition, or damage; b) isolating muscle-derived extracellular vesicles from cells or tissues of the subject or in vivo or in vitro model at two or more time points before, during, and/or after the providing of the candidate therapeutic agent and/or comparing a single time point from treated and untreated model experimental units/groups; c) characterizing one or more components within or on the extracellular vesicles at each time point; and d) identifying an effective therapeutic agent for the muscle-related disorder, condition, or damage based on changes in the characteristics of the one or more components or absence of one or more components within or on the extracellular vesicles at each time point. In some embodiments, 1, 2, 3, 4, or 5 or more components are characterized.

Each of the screening methods may be carried out in vitro, e.g., in cultured cells, e.g., cell lines or primary cells. In some embodiments, the cells are primary muscle cells or muscle cell lines. In some embodiments, the cells are muscle satellite cells, primary muscle cells, HEK293 cells, HEK293T cells, CAP cells, mesenchymal stem cells, immune cells, or any combination thereof.

Each of the screening methods may be carried out in vivo, e.g., in an animal model of a disease, condition, or damage, or in a subject, e.g., in a clinical trial. The EVs may be isolated from cell culture medium in in vitro studies or from a bodily fluid in in vivo studies before, during, and/or after the candidate therapy or candidate therapeutic agent is provided to the cells, animals, or subjects. The components of the EVs may then be characterized to identify desirable changes, e.g., increasing or decreasing amounts, appearance or disappearance of variants or mutants, etc.

The one or more components may be any components that are biomarkers of a muscle-related disorder, condition, or damage. In some embodiments, the one or more components are proteins, DNAs, RNAs, and/or organelles. The one or more components may be any of the proteins, DNAs, or RNAs listed in Table 2 or any combination thereof. Characterization of the components may include determining any characteristic of the component that serves as a biomarker providing information regarding the muscle-related disorder, condition, or damage. In some embodiments, characterizing the one or more components within the EVs comprises determining the presence, absence, abundance, molecular weight and/or sequence of the one or more components.

The bodily fluid may be any bodily fluid in which muscle-derived EVs can be found, including without limitation, blood, serum, plasma, urine, saliva, sputum, CSF, sweat, milk, ascites, cyst fluid, pleural fluid, peritoneal fluid, intestinal fluid, fecal fluid, or tears.

The muscle-derived EVs may be isolated, for example, by the methods disclosed above, e.g., using a capture agent such as the ones disclosed in Table 1.

Therapeutic Methods Using Extracellular Vesicles

One aspect of the invention relates to the use of EVs as delivery vehicles for therapeutic agents. In some embodiments, the EVs may naturally contain the therapeutic agents. In other embodiments, the cells from which the EVs are derived may be modified to contain the therapeutic agents or higher levels of the therapeutic agent, which then end up in the EVs. The use of EVs to deliver therapeutic agents such as viral vectors that may raise an immune response may prevent or diminish the immune response against the vector. Additionally, EVs can cross most membranes, including the blood brain barrier, so they may be used to deliver therapeutic agents to the brain as well as other tissues and organs. Another advantage is the ability of EVs to rapidly deliver therapeutic agents to a tissue, e.g., within 24 hours.

Thus, one aspect of the invention relates to a method of treating a disorder, condition, or damage in a subject in need thereof, comprising: a) isolating extracellular vesicles comprising one or more therapeutic agents from cell culture medium of cultured cells; and b) administering a therapeutically effective amount of the extracellular vesicles to the subject; thereby treating the muscle-related disorder, condition, or damage. In some embodiments, the disorder, condition, or damage is a neuromuscular disorder, condition, or damage or a neurological disorder, condition, or damage. In some embodiments, the disorder, condition, or damage is a muscle-related disorder, condition, or damage.

The cultured cells may be any cells that comprise a therapeutic agent that is present in EVs derived from the cells. In some embodiments, the cells are primary muscle cells or muscle cell lines. In some embodiments, the cells are muscle satellite cells, primary muscle cells, HEK293 cells, HEK293T cells, CAP cells, mesenchymal stem cells, immune cells, or any combination thereof.

The therapeutic agent may be any therapeutic agent know or later discovered to be effective for treatment of a disorder, condition, or damage, e.g., a neurological or muscle-related disorder, condition, or damage. In some embodiments, the therapeutic agent may be a protein, RNA (e.g., mRNA, siRNA, microRNA, lncRNA), DNA, expression vector (e.g., plasmid or viral vector (e.g., AAV), organelle, CRISPR complex, exon skipping compound (e.g., a morpholino exon skipping compound), or any combination thereof. In some embodiments, the therapeutic agent is a naturally occurring protein (e.g., dystrophin) or a nucleic acid encoding the naturally occurring protein. In some embodiments, the therapeutic agent is a non-naturally occurring protein (e.g., a fragment or modified version such as a minidystrophin or microdystrophin) or a nucleic acid encoding the non-naturally occurring protein.

In some embodiments, the cells have been modified to contain a higher level of the one or more therapeutic agents than unmodified cells. In some embodiments, the one or more therapeutic agents or a nucleic acid encoding the one or more therapeutic agents have been introduced into the cells, e.g., by transfection, transduction, infection, electroporation, or any combination thereof. In some embodiments, the cells have been modified to produce an expression vector, e.g., a plasmid vector or a viral vector. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic acid-protein complexes, and biopolymers.

In some embodiments, the cells have been modified to contain a targeting agent that will target the extracellular vesicles to a target tissue. In some embodiments, the targeting agent is a transmembrane protein. In some embodiments, the target tissue is muscle. The targeting agent may be, without limitation, one of the proteins listed in Table 1. In some embodiments, the target tissue is the central nervous system and/or peripheral nervous system. Molecules that can be used to target products to the nervous system are well-known in the art. Examples include, without limitation, SNAP25, Tau, NF-L, GFAP, MBP, OMGP, EAAT1, PLP, LCAM1, and CD13.

In some embodiments, the therapeutic agent itself can provide targeting. For example, viral vectors have particular tropism patterns that can be used advantageously to deliver cargo to specific tissues, e.g., muscle or central nervous system. Selecting an appropriate serotype of a viral vector, e.g., AAV vector, may provide the desired targeting, e.g., to muscle or the brain.

The EVs may be isolated from the cell medium by any method known in the art. For example, the EVs may be collected by centrifugation and filtration. In some embodiments, the EVs may be isolated using a capture agent as described above.

The disorder, condition, or damage may be any disorder, condition, or damage for which a therapeutic agent is known. Non-limiting examples of disorders, conditions, or damage and the proteins and nucleic acids associated with them are listed in Table 2. The one or more therapeutic agents may be any of the proteins and nucleic acids listed in Table 2 or a vector delivering the protein (e.g., dystrophin) or protein fragment or modified version thereof (e.g., minidystrophin or microdystrophin)-encoding nucleic acid in any combination.

In some embodiments, the EVs are obtained from HEK293 cells. HEK293 cells have been determined to produce EVs comprising a variety of components that can be used as therapeutic agents. One surprising component of EVs is full-length dystrophin protein and full-length dystrophin mRNA, making the EVs ideal for treatment of muscular dystrophies associated with mutations in dystrophin. Table 3 lists components (protein and/or RNA) found in HEK293-derived EVs that could be used as therapeutic agents, along with the disorder associated with each component.

TABLE 3

| Protein | Gene | Disorder | Protein in EVs | RNA in EVs |
|---|---|---|---|---|
| Tripartite motif-containing protein 32 | TRIM32 | Limb girdle muscular dystrophy type 2H | X | X |
| Utrophin | UTRN | | X | X |
| Lamin B1 | LMNB1 | Adult-onset autosomal dominant leukodystrophy | X | X |
| Lamin Al | LMNA | Emery-Dreifuss muscular dystrophy 2 | X | X |
| Dystrophin | DMD | Duchenne muscular dystrophy | X | X |

TABLE 3-continued

| Protein | Gene | Disorder | Protein in EVs | RNA in EVs |
|---|---|---|---|---|
| Neurofibromin | NF1 | Neurofibromatosis type 1 | X | X |
| Tropomyosin 3 | TPM3 | Nemaline myopathy 1 | | X |
| Tropomyosin 2 | TPM2 | Nemaline myopathy 4 | | X |
| Troponin T1 | TNNT1 | Nemaline myopathy 5 | | X |
| Selenoprotein N | SEPN1 | Rigid spine muscular dystrophy 1 | | X |
| Sarcoglycan beta | SCGB | Beta sarcoglycanopathy | | X |
| Methylmalonyl-CoA mutase | MUT | Methylmalonic acidemia | | X |
| Cobalamin C | MMACHC | Methylmalonic academia Homocysteinuria | | X |
| Lamin B2 | LMNB2 | Progressive myoclonic epilepsy 9 | | X |
| Frataxin | FXN | Friedreich's ataxia | | X |
| Cofilin 2 | CFL2 | Nemaline myopathy 7 | | X |
| Alpha dystroglycan | DAG1 | Dystroglycanopathy (many variants) | X | |
| Contactin 1 | CNTN1 | Compton-North congenital myopathy | X | |
| Cystic fibrosis modifier 1 | CFM1 | Susceptibility to meconium ileus in cystic fibrosis | X | |
| Bridging integrator 1 | BIN1 | Centronuclear myopathy 2 | X | |
| β-hexosaminidase A | HEXA | Tay-Sachs | X | |
| A1,4-glucosidase (acid maltase) | GAA | Pompe | X | |
| Dystrobrevin alpha | DTNA | | X | |
| Dystrobrevin beta | DTNB | | X | |
| Dystonin | DST | | X | |

In some embodiments, rather than delivering the EVs containing the therapeutic agents in the EVs, the EVs can be isolated and lysed to obtain the therapeutic agents and then the therapeutic agents are delivered to the subject. In these embodiments, the isolation of the therapeutic agents may provide an increased yield, recovery, and/or purity compared to isolating the therapeutic agents directly from cells. For example, viral vectors (e.g., AAV vectors) may be isolated from EVs rather than directly from the producer cells.

In particular embodiments, the present invention provides a pharmaceutical composition comprising EVs of the invention in a pharmaceutically acceptable carrier. In some embodiments, the present invention provides a pharmaceutical composition comprising EVs of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

The terms "patient," "subject," "individual," and the like are used interchangeably herein, and refer to any animal, or cells thereof whether in vitro or in situ, amenable to the methods described herein. In a preferred embodiment, the patient, subject, or individual is a mammal. In some embodiments, the mammal is a mouse, a rat, a guinea pig, a non-human primate, a dog, a cat, or a domesticated animal (e.g. horse, cow, pig, goat, sheep). In some embodiments, the patient, subject or individual is a human. As a further option, the subject can be a laboratory animal and/or an animal model of disease.

Human subjects include neonates, infants, juveniles, and adults. For these purposes, human subjects may also include reproductive cells, either fertilized or not, and developing conceptus through all stages of development prior to being identified as a neonate. Optionally, the subject is "in need of" the methods of the present invention, e.g., because the subject has or is believed at risk for a disorder including those described herein or that would benefit from the delivery of EVs including those described herein.

The cell(s) into which the EVs of the invention can be introduced may be of any type, including but not limited to neural cells (including cells of the peripheral and central nervous systems, in particular, brain cells such as neurons, oligodendrocytes, glial cells, astrocytes, Schwann cells), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, immune cells, and the like. Alternatively, the cell may be any progenitor cell. As a further alternative, the cell can be a stem cell (e.g., neural stem cell, liver stem cell). Moreover, the cells can be from any species of origin, as indicated above.

The EVs of the invention may be introduced to cells in vitro for the purpose of administering the modified cell to a subject. In particular embodiments, the cells have been removed from a subject, the EVs of the invention are introduced therein, and the cells are then replaced back into the subject. Methods of removing cells from subject for treatment ex vivo, followed by introduction back into the subject are known in the art (see, e.g., U.S. Pat. No. 5,399,346). Alternatively, EVs of the invention are introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the therapeutic agent contained in the cell, the mode of administration, and the like. Typically, at least about $10^2$ to about $10^8$ or about $10^3$ to about $10^6$ cells will be administered per dose in a pharmaceutically acceptable carrier. In particular embodiments, the cells comprising the EVs are administered to the subject in an effective amount in combination with a pharmaceutical carrier.

In certain embodiments, the EVs of the invention are administered to a subject in need thereof as early as possible in the life of the subject, e.g., as soon as the subject is diagnosed with aberrant expression or activity of a nucleic acid or protein of interest. In some embodiments, the EVs are administered to a newborn subject, e.g., after newborn screening has identified aberrant expression or activity of a nucleic acid or protein of interest. In some embodiments, the EVs are administered to a fetus in utero, e.g., after prenatal screening has identified aberrant expression or activity. In some embodiments, the EVs are administered to a subject as soon as the subject develops symptoms associated with aberrant expression or activity of a nucleic acid or protein of interest, or is suspected or diagnosed as having aberrant expression or activity of a nucleic acid or protein of interest. In some embodiments, the EVs are administered to a subject before the subject develops symptoms associated with aberrant expression or activity of a nucleic acid or protein of interest, e.g., a subject that is suspected or diagnosed as having aberrant expression or activity but has not started to exhibit symptoms.

A further aspect of the invention is a method of delivering the EVs and/or pharmaceutical composition of the invention to a subject. In particular embodiments, the method comprises a method of delivering EVs to an animal subject, the method comprising: administering an effective amount of EVs according to the invention to an animal subject. Administration of the EVs of the present invention to a human subject or an animal in need thereof can be by any means known in the art. Optionally, the EVs are delivered in an effective dose in a pharmaceutically acceptable carrier.

Dosages of EVs to be administered to a subject will depend upon the mode of administration, the disease or condition to be treated, the individual subject's condition, the particular EVs, and the therapeutic agent to be delivered, and can be determined in a routine manner.

In particular embodiments, more than one administration (e.g., two, three, four or more administrations) may be employed to achieve the desired level of therapeutic agent over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, or brain). Administration can also be to a tumor (e.g., in or near a tumor or a lymph node). The most suitable route in any given case will depend on the nature and severity of the condition being treated and on the nature of the particular vector that is being used.

In some embodiments, the EVs administered to the central nervous system (CNS), the peripheral nervous system, or both.

In some embodiments, the vector is administered directly to the CNS, e.g., the brain or the spinal cord. Direct administration can result in high specificity of transduction of CNS cells, e.g., wherein at least 80%, 85%, 90%, 95% or more of the transduced cells are CNS cells. Any method known in the art to administer EVs directly to the CNS can be used. The EVs may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The EVs may also be administered to different regions of the eye such as the retina, cornea or optic nerve. The EVs may be delivered into the cerebrospinal fluid (e.g., by lumbar puncture) for more disperse administration of the vector.

The EVs may be administered to the desired region(s) of the CNS by any route known in the art, including but not limited to, intrathecal, intracerebral, intraventricular, intranasal, intra-aural, intra-ocular (e.g., intra-vitreous, sub-retinal, anterior chamber) and peri-ocular (e.g., sub-Tenon's region) delivery or any combination thereof.

The EVs may be administered in a manner that produces a more widespread, diffuse transduction of tissues, including the CNS, the peripheral nervous system, and/or other tissues.

Typically, the EVs will be administered in a liquid formulation by parenteral (e.g., intravenous injection or direct injection (e.g., stereotactic injection) to the desired region or compartment in the CNS and/or other tissues. In some embodiments, the EVs can be delivered via a reservoir and/or pump. In other embodiments, the EVs may be provided by topical application to the desired region or by intra-nasal administration of an aerosol formulation. Administration to the eye or into the ear, may be by topical application of liquid droplets. As a further alternative, the EVs may be administered as a solid, slow-release formulation.

Injectables can be prepared in conventional forms, either as liquid solutions or suspensions, solid forms suitable for solution or suspension in liquid prior to injection, or as emulsions. Alternatively, one may administer the EVs in a local rather than systemic manner, for example, in a depot or sustained-release formulation.

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing EVs of the present invention to a carrier capable of withstanding degradation by digestive enzymes in the gut of an animal or human. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical compositions according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 μg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, e.g., *Pharm. Res.* 3:318 (1986)) and typically take the form of an optionally buffered aqueous solution of the composition of this invention. Suitable formulations can comprise citrate or bis\tris buffer (pH 6) or ethanol/water.

The EVs disclosed herein may be administered to the lungs of a subject by any suitable means, for example, by administering an aerosol suspension of respirable particles comprised of the EVs, which the subject inhales. The respirable particles may be liquid or solid. Aerosols of liquid particles comprising the EVs may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the vectors may likewise be produced with any solid particulate medicament aerosol generator, by techniques known in the pharmaceutical art.

Compositions and Kits

A further aspect of the invention relates to compositions and kits for carrying out the methods of the invention. Thus, in one aspect, the invention relates to a composition comprising a capture agent for capturing extracellular vesicles. The capture agent may be conjugated to a solid support, e.g., a bead, e.g., a magnetic bead. In other embodiments, the solid support may be a plate or a well in a plate.

The capture agent may be any of the capture agents described above, e.g., an antibody, antibody fragment, antibody derivative, aptamer, or aptamer-based biosensor. In some embodiments, the capture agent may be one of the agents listed in Table 1.

The composition may further comprise a suitable carrier, e.g., a physiologically compatible solution or buffer, e.g., saline.

Another aspect of the invention relates to a composition comprising extracellular vesicles comprising one or more therapeutic agents, the extracellular vesicles isolated from cell culture medium of cultured cells. In some embodiments, the cells are muscle satellite cells, primary muscle cells, HEK293 cells, HEK293T cells, CAP cells, mesenchymal stem cells, immune cells, or any combination thereof. In some embodiments, the EVs are non-naturally occurring EVs, e.g., EVs derived from modified (non-naturally occurring) cells.

The therapeutic agent may be any therapeutic agent known to be effective for treatment of a muscle-related disorder, condition, or damage. In some embodiments, the therapeutic agent may be a protein, RNA (e.g., mRNA, siRNA, microRNA, lncRNA), DNA, expression vector (e.g., plasmid or viral vector (e.g., AAV), organelle, CRISPR complex, exon skipping compound, or any combination thereof.

In some embodiments, the EVs are isolated from cells that have been modified to contain a higher level of the one or more therapeutic agents than unmodified cells. In some embodiments, the one or more therapeutic agents or a nucleic acid encoding the one or more therapeutic agents or vectors (e.g., viral vectors) delivering a nucleic acid encoding one or more therapeutic agents have been introduced into the cells, e.g., by transfection, transduction, infection, electroporation, or any combination thereof. In some embodiments, the cells have been modified to produce an expression vector, e.g., a plasmid vector or a viral vector.

Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic acid-protein complexes, and biopolymers.

In some embodiments, the EVs are isolated from cells that have been modified to contain a targeting agent that will target the extracellular vesicles to a target tissue. In some embodiments, the targeting agent is a transmembrane protein. In some embodiments, the target tissue is muscle. The targeting agent may be, without limitation, one of the proteins listed in Table 1. In some embodiments, the target tissue is the central nervous system and/or peripheral nervous system. Molecules that can be used to target products to the nervous system are well-known in the art. Examples include, without limitation, SNAP25, Tau, NF-L, GFAP, MBP, OMGP, EAAT1, PLP, LCAM1, and CD13.

The one or more therapeutic agents may be any of the proteins or nucleic acids listed in Table 2 or any combination thereof. In some embodiments, the therapeutic agent is a naturally occurring protein (e.g., dystrophin) or a nucleic acid encoding the naturally occurring protein. In some embodiments, the therapeutic agent is a non-naturally occurring protein (e.g., a fragment or modified version such as a minidystrophin or microdystrophin) or a nucleic acid encoding the non-naturally occurring protein.

An additional aspect of the invention relates to a kit for capturing extracellular vesicles, the kit comprising a capture agent. The capture agent may be conjugated to a solid support, e.g., a bead, e.g., a magnetic bead. In other embodiments, the solid support may be a plate or a well in a plate. In some embodiments, the capture agent and the solid support are separate, to be conjugated during the capture method.

The capture agent may be any of the capture agents described above, e.g., an antibody, antibody fragment, antibody derivative, aptamer, or aptamer-based biosensor. In some embodiments, the capture agent may be one of the agents listed in Table 1.

The kit may further comprise other components, e.g., a suitable carrier for the capture agent, e.g., a physiologically compatible solution or buffer, e.g., saline. Other components may include, without limitations, containers, vails, plates, reagents, buffers, dyes, markers, controls, and/or instructions for carrying out the methods of the invention.

Having described the present invention, the same will be explained in greater detail in the following examples, which are included herein for illustration purposes only, and which are not intended to be limiting to the invention.

EXAMPLES

Example 1: Satellite Cell-Derived Extracellular Vesicles Reverse Peroxide-Induced Mitochondrial Dysfunction in Myotubes Satellite cells (SCs) are skeletal muscle stem cells and play a central role in skeletal muscle remodeling. Upon injury to muscle, SCs are activated, proliferate, and differentiate into myoblasts and then fuse into the preexisting muscle cells to facilitate regeneration. Due to their role in regeneration and repair, SCs may provide therapeutic benefit to a range of muscle disorders and pathologies. Current strategies in SC-based therapies have focused primarily on the isolation, culture, and transplantation of SCs into dystrophic animals and patients. Although initially promising, limitations exist in many common SC therapeutic approaches and this strategy remains largely unsuccessful. For example, since skeletal muscle is the most abundant tissue in humans, a very high number of SCs are likely required to treat systemic muscle conditions, though the number of SCs required to achieve a lasting therapeutic benefit is equivocal. Further, generating the large number of SCs needed requires expanding SCs ex vivo; however, the capacity to expand isolated SCs is limited before myogenic potential rapidly declines.

Recent evidence indicates extracellular vesicles (EVs) may independently convey SC-mediated benefits. Extracellular vesicles are small, lipid-coated vesicles that contain cellular cargo and are generally classified by size as exosomes, microvesicles, and large EVs (apoptotic bodies). Most, if not all, cell types including muscle cells release EVs. Extracellular vesicles participate in paracrine and endocrine-like signaling via the selective packaging of specific molecular cargo that is delivered into nearby and distant recipient cells. Recent evidence indicates that SC-EVs regulate muscle remodeling, at least in part, via delivery of miR-206 to fibrogenic cells. Therefore, SC-EVs taken up by recipient muscles cells could provide therapeutic benefit for myopathies.

Mitochondria are essential for cellular energy production and overall viability. In skeletal muscle cells, mitochondrial dysfunction is associated with increased reactive oxygen species (ROS) generation, impaired calcium handling, atrophy and weakness. Thus, mitochondria may be a viable therapeutic target in the treatment of muscle disorders caused by or complicated by mitochondrial dysfunction, such as Duchenne muscular dystrophy (DMD), cachexia, disuse atrophy, sarcopenia, etc.

Hence, the purpose of this investigation was to determine the extent to which SC-EVs would restore muscle mitochondrial function following an acute oxidative insult. It was hypothesized that SC would release a full complement of EVs (exosomes, apoptotic bodies, and large EVs), that these EVs could enter muscle fibers, and that these EVs would attenuate oxidative stress-mediated dysfunction.

Material and Methods

Animals: All animal procedures were approved by the IACUC at the University of Delaware. C57BL/6 mice (n=8, 4-6 weeks of age, mixed male and female) were anesthetized using isoflurane gas throughout the dissection protocol.

Isolation of Satellite Cells: Briefly, all the muscles of the lower limb were removed from both limbs and stored in wash buffer on ice. The muscles were then minced into a slurry, containing pieces approximately 3 mm in diameter. The tissue was then transferred to dissociation buffer and incubated at 37° C. for 1 hour, while being mixed every 5-10 min. This was followed by a wash step before adding stock collagenase II and stock dispase to the solution. This solution was then incubated for an additional half hour at 37° C. while mixing. A 10 ml, 20 gauge needle was then used to triturate the solution. This was followed by an additional wash before the solution was run through a 40 µm filter. Two washes through the filter were then performed. The cells were then pelleted by centrifugation and all of the media was aspirated off. A Satellite Cell MACS solution (Miltenyi Biotec) was then used to isolate the SCs from the cell suspension via magnetic separation.

Satellite Cell Culture: SCs were isolated using a commercially available kit (Satellite Cell Isolation Kit, Bergisch Gladbach, Germany) and were seeded on MATRIGEL® coated 6-well plates. Varying seeding densities were used initially with an optimal seeding density found between 135,000-180,000 cells/well ($1.5 \times 10^4$-$2 \times 10^4$ cells/cm$^2$). The cells were grown in vesicle-free expansion media, made as specified by manufacturer's instructions, for six days, with media being replaced and collected each day.

Myotube Cell culture: C2C12 myoblasts were cultured on an 8-chamber cover glass slide and differentiated after proliferating to 90-100% confluency. Following 5 days in differentiation media, the myoblasts had adequately fused to form myotubes.

EV isolation, Labeling, and Uptake: EVs were isolated from the SC culture media using EXOQUICK® TC (System Bioscience, Palo Alto, USA), following the manufacturer's instructions and resuspended in 1×PBS for long term storage at −80° C. Isolated EVs were labeled using 10 µM carboxyfluorescein succinimidyl ester (CFSE) dye in PBS for 2 hr at 37° C. Following the incubation period, EXOQUICK® TC was used via manufacturer's instructions to re-pellet and isolate the labeled-EVs. The labeled EVs were then resuspended in 100 µl PBS and 50 µg labeled SC EVs were added to the cells' vesicle free differentiation media in four of the chambers and incubated at 37° C. for 24 hours. After 22 hours of incubation with the labeled EVs, LYSOTRACKER® red DND-99 (ThermoFisher Scientific, Waltham, USA) was added to two of the EV-treated chambers in addition to two separate chambers. Two chambers were also treated with a filtered PBS/CFSE dye solution as a vehicle control group.

Time Course Analysis of Labeled-SC EV-Protein Uptake in C2C12: The average spot intensity measurement on the Cellinsight CX7 (Thermo Fisher Scientific, Waltham, USA) was used to analyze the uptake of CFSE fluorescently-labeled SC EV protein delivered by C2C12 myotubes. Briefly, C2C12 were cultured in a 96 well micro-clear plate (Greiner Bio-One, Monroe, USA). Separately, EVs were isolated from SC culture media and labeled via incubation with 10 µM CFSE at 37° C. for 2 hr. Excess dye was removed by re-isolating the labeled-EVs using EXOQUICK® TC. The labeled EVs were then incubated in the culture media of C2C12 in the 96 well plate for 5 min, 30 min, 1 hr, 2 hr, 6 hr, 24 hr and 48 hr. The cells were then washed with PHEM buffer to remove any labeled protein that was not incorporated into the cell and fixed in 4% PFA for 10 min at room temperature. The plate was then analyzed on the Cellinsight CX7 to measure the differences in fluorescent intensity, indicative of protein uptake, at the various timepoints.

EV protein localization: C2C12 cells exposed to 24 hr of labeled-SC EV exposure were washed with PHEM buffer and fixed using PHEM fixative containing 4% paraformaldehyde (PFA). The fixed preparations were then imaged on the LSM-880 confocal microscope system (Zeiss, Oberkochen, Germany) to obtain representative images of labeled SC EV protein uptake in C2C12.

Live Cell Metabolic Assay: C2C12 myotubes were cultured on 8-well Seahorse culture plates (Agilent, Santa Clara, USA). The cells in each well were then divided into four different groups: control (no treatment), $3.12 \times 10^8$ SC EV, 50 µM $H_2O_2$, or $H_2O_2$ with subsequent SC EV treatment. In each group, the treatments were administered by adding the compounds of interest to the culture media prior to dispensing the media in the wells. Each treatment was conducted for 24 hr. Following the treatment period, the media was removed, the cells were washed with prepared Seahorse Assay Media (Agilent, Santa Clara, USA), and then replaced with the Assay Media. The cells were incubated in the assay media for 45 mins in a $CO_2$-free 37° C. incubator, and then analyzed on the Agilent Seahorse platform per manufacturer instructions.

Statistical Analyses: Group sample size was determined by performing a power analysis of preliminary data. When results from two groups were compared, a t-test was used to test for significance. When results from more than two groups were compared, a one-way ANOVA was used to determine overall significance. When appropriate, a post hoc Tukey honestly significant difference (HSD) test was performed. Differences in results were considered significant when $P \leq 0.05$. For each outcome, at least 3-5 samples per treatment group, acquired from $\geq 3$ independent experiments, were quantified and analyzed.

Results

Characterization of SC-EVs: To determine the size and number of EVs released from SCs, the media was collected from cultured SCs 24 hours after a media change. EVs were then isolated from media and quantified via nanoparticle tracking analysis. Over this 24 hour period, on average, each SC released approximately $2.00 \times 10^5 \pm 8.04 \times 10^3$ EVs (FIG. 1). Further, since numerous EV subpopulations exist, we examined the size distribution of the SC-EVs. Our data show an average size of 125.7±1.7 nm, although the majority of the EVs released were 99.3±2.6 nm, a size that is indicative of exosomes.

SC-EVs rapidly deliver protein into myotubes: Next, we sought to demonstrate that SC-EVs could deliver cargo to recipient muscle cells. EVs were isolated from media 24 hrs following a media change. Protein in SC-EVs was labeled with carboxyfluorescein succinimidyl ester (CFSE). SC-EVs containing fluorescently-tagged protein were then delivered to myotubes and then visualized within recipient cells. Following 24 h of incubation we demonstrated fluorescently labeled protein was present in recipient cells. Hence, SC-EVs are capable of robust delivery of protein when supplemented in the media of cultured myotubes. Next, we further elucidated characteristics of protein delivery over a 48 hour period. This time course analysis demonstrated significant delivery of SC-EV protein relative to control as early as 2 hours after exposure and for the remainder of the 48 hour incubation period ($P<0.05$), with the most robust delivery of labeled protein observed at 24 hours after exposure (FIGS. 2A-2G).

SC-EVs reverse peroxide-induced mitochondrial dysfunction: As it was clear that SC-EVs effectively delivered protein to recipient muscle cells we next explored the potential of these EVs to attenuate dysfunction caused by acute oxidative stress. Mitochondrial respiration was measured in C2C12 myotubes under control conditions and following a 24 h treatment with 50 µM hydrogen peroxide ($H_2O_2$). $H_2O_2$ exposure resulted in a 38.4% decline in peak mitochondrial respiration as well as a 46.1% reduction in spare respiratory capacity ($p<0.05$) (FIGS. 3A-3E). Subsequent treatment with SC-EVs ($3.12 \times 10^8$ SC-EV; 24 h) following $H_2O_2$ exposure fully reversed $H_2O_2$-mediated dysfunction in peak mitochondrial respiration. Similarly, $H_2O_2$-mediated losses in spare respiratory capacity were also abrogated by SC-EVs. Finally, we also included myotubes treated with SC-EVs without oxidative insult. Here, we discovered that SC-EVs augmented peak mitochondrial function by 7.6% and spare respiratory capacity by 4.1% in healthy myotubes.

Discussion

Extensive literature exists on the potential of SCs as therapeutic agents to combat a variety of myopathies. The therapeutic application of these cells is attributed their ability to differentiate into myoblasts and fuse into damage fibers to support regeneration.

Evidence suggests EVs released from mesenchymal stem cells confer many of the same regenerative benefits as the cells themselves. Given the potential of SC-EVs to impact adult fibers, the purpose of this investigation was to determine the extent to which SC-EVs attenuate mitochondrial dysfunction caused by acute oxidative stress. We found SCs release approximately 200,000 EVs/day/cell and that adult myotubes take up large amounts of SC-EVs. Finally, we also discovered EVs reverse mitochondrial dysfunction caused by oxidative stress.

Mitochondria are critical in cellular energy production as well as the regulation of overall cellular viability. Mitochondrial dysfunction plays a central role in numerous muscular disorders and pathologies, including DMD. For example, previous work demonstrates that mitochondrial dysfunction, attributed by impaired oxidative phosphorylation and elevated oxidant production, contribute to early stage pathology in the D2.mdx mouse model. Additionally, in the mdx mouse model, mitochondrial dysfunction is one of the earliest cellular consequences of dystrophin deficiency and is associated with the inability of dystrophic muscle cells to respond to sarcolemmal damage. Adverse alterations in mitochondrial morphology and function are also known to play a central role in the pathology of muscle dysfunction and wasting in murine models of cancer cachexia, attributed to decreased ATP production and uncoupling of oxidative phosphorylation. It is also well-documented that mitochondrial dysfunction contributes to disuse atrophy. For example, previous work demonstrates that a mitochondrial-targeted antioxidant was able to ameliorate ventilation-induced diaphragm weakness. Given these data, SC-EVs may present a viable treatment option for a host of muscle pathologies caused by a variety of dysfunctions that include mitochondrial dysfunction as part of the disease sequelae. This approach has distinct advantages over cell transplantation including, most notably, the abundance of EVs released and the efficiency with which they deliver molecular cargo. Further, release of SC-EVs can be stimulated via extracellular GTP and oxidative stress and cargo can be altered by manipulation of SC gene expression, demonstrating the ability to manipulate the number of EVs released and molecular cargo.

In summary, these data suggest that satellite cells release large amounts of varied EVs. Further, these SC-EVs rapidly deliver molecular cargo to mature myotubes. Finally, we discovered that these SC-EVs reverse oxidative stress-mediated mitochondrial dysfunction and restore myotube energetic phenotype. Given this profound therapeutic response and the role of oxidative stress in a host of muscle pathologies, SC-EVs may be an effective, simple, safe, and scalable therapeutic approach.

Example 2: Determination of Surface Proteins on Muscle-Derived Extracellular Vesicles EVs from human plasma or the media of mouse skeletal muscle cells were incubated with trypsin or proteinase K to remove extracellular protein epitopes. EVs were subsequently re-isolated and the pellets (containing EVs) and supernatants (containing shaved proteins) were sent to System Biosciences (Mountain View, CA) where EV total and surface protein profiling was performed according to their standard procedures. Identified membrane proteins known or predicted to be specific or highly enriched in skeletal muscles were selected as potential candidates to be utilized to captured muscle-derived EVs from bodily fluid. To validate proteins were in fact on the surface of the EVs, EVs from blood or media of cultured mouse muscle cells were incubated with antibodies conjugated to magnetic beads. Beads with bound muscle-derived EVs were isolated via magnetic separation, stained with CFSE, and imaged via flow cytometry. Data were analyzed as a histogram plot (GREEN-Log) to determine MFI signal (capture protein+ EV content for a given sample. Table 1 lists proteins validated by this method.

Example 3: Isolation and Characterization of Extracellular Vesicles from HEK293 Cells EVs were isolated from the culture media of HEK293 cells using EXOQUICK® (System Bioscience, Palo Alto, USA), following the manufacturer's instructions and resuspended in 1×PBS containing protease inhibitor cocktails.

Figure 4:
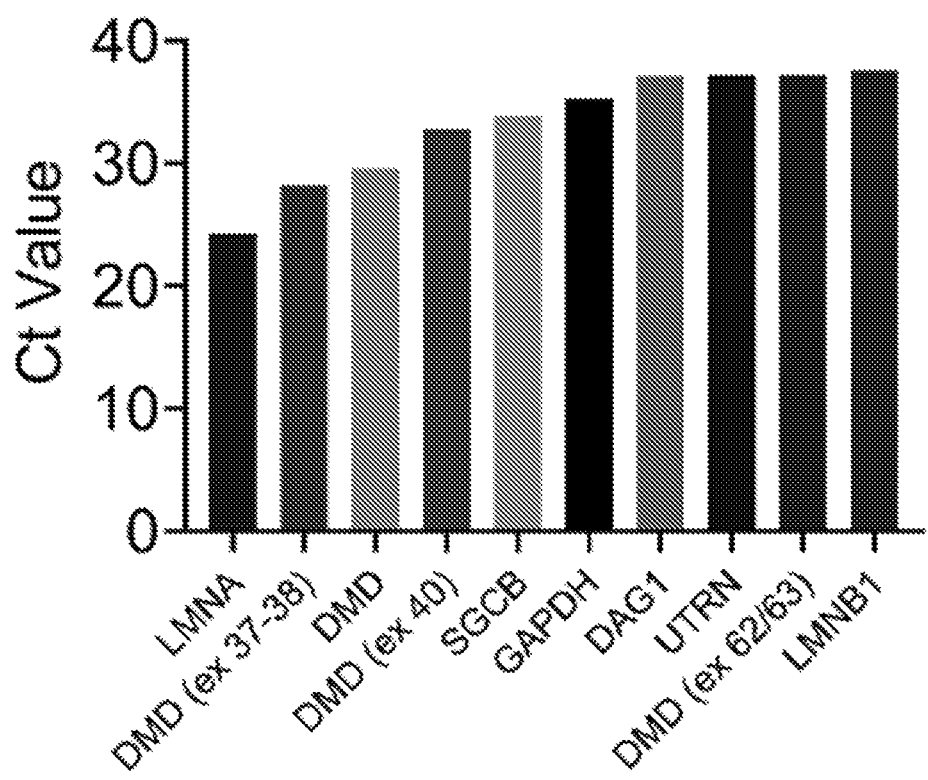
FIG. 4 shows raw qPCR data verifying packaging of mRNA into EVs. The lower the Ct (threshold cycle) indicates earlier amplification and more mRNA abundance. Different primers for different dystrophin exons were utilized to verify full length dystrophin.

The presence of mRNAs in the EVs was validated using qPCR. RNA was isolated from the EVs by lysing the EVs and cDNA was synthesized from RNA using the qScript cDNA synthesis kit (Quantabio, Beverly, MA, USA). Equal amounts of cDNA were used to perform qPCR analysis. The results are shown in FIG. 4, indicating numerous mRNAs that were present in the EVs.

The HEK293 EVs were analyzed by proteomics using mass spectroscopy (Bioproximity, Manassas, VA) to determine the proteins present in the EVs and by next generation sequencing (System Biosciences, Mountain View, CA) to determine the RNAs present in the EVs. Exemplary results are listed in Table 3.

Example 4: Extracellular Vesicles Comprising AAV Particles

Figure 5:
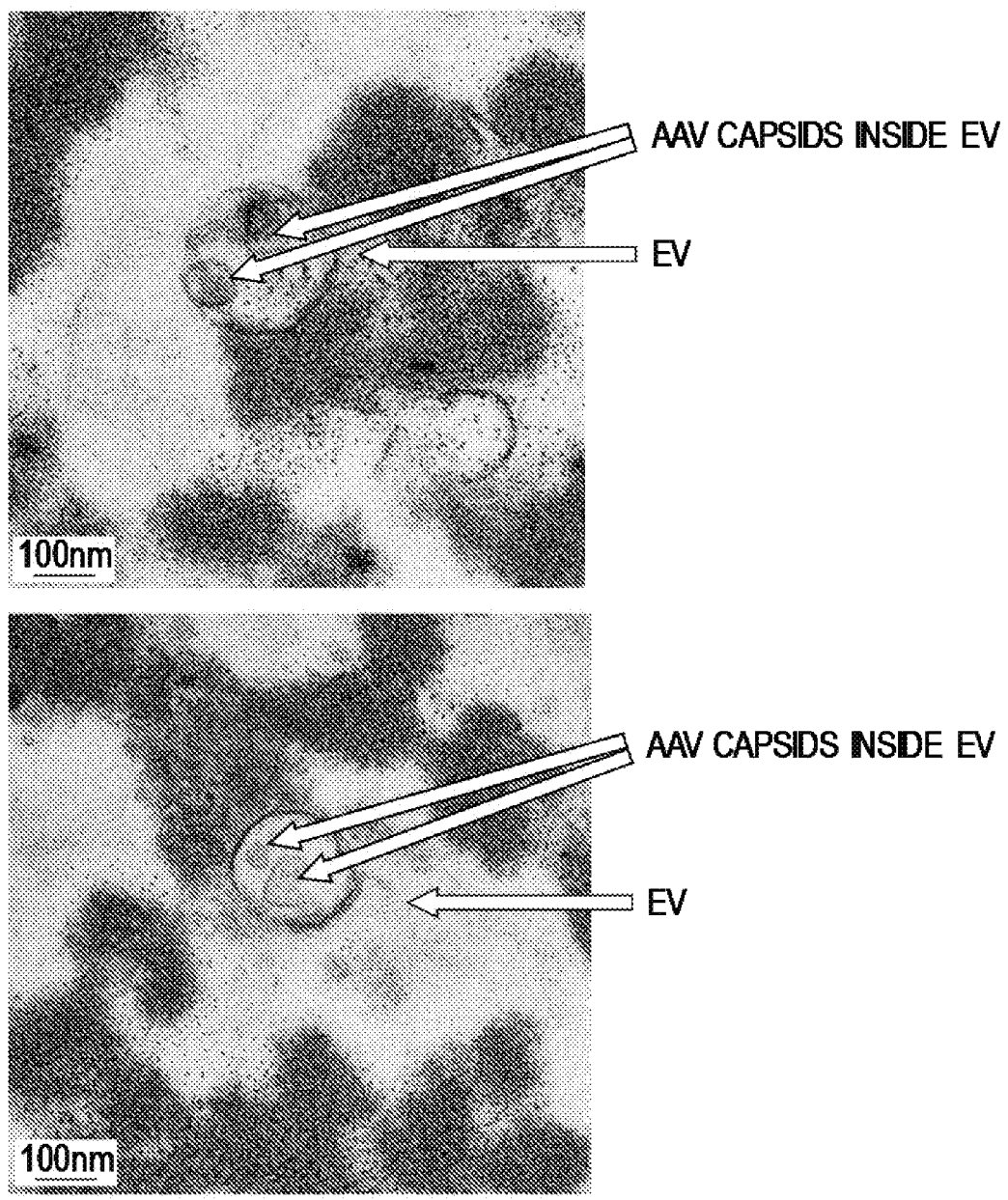
FIG. 5 shows electron micrographs of EVs that contain AAV.

HEK293 cells in vesicle depleted medium were transduced with AAV6-GFP (Capsid from AAV6 and ITR from AAV expressing eGFP under the control of a CMV promoter) at 15,000 viral genome copies of per cell. After 4 and 12 hours media was removed, cells were washed three times with phosphate buffered saline, and EV free media was added to the cells. After 48 hours cells were collected and EVs were isolated using EXOQUICK® and saved in in fixative for transmission electron microscopy. In FIG. 5 transmission electron microscopy verifies the presence of AAV in EVs.

Figure 6:
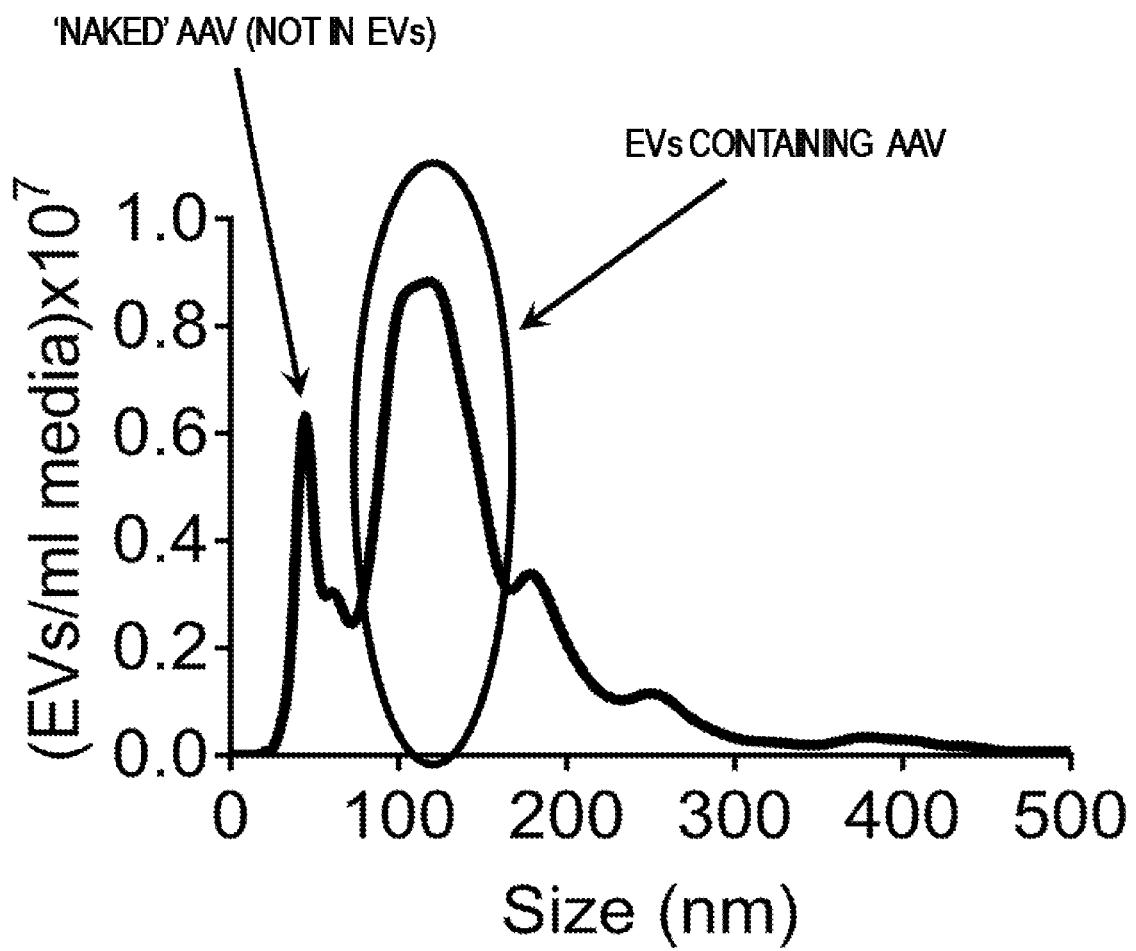
FIG. 6 shows cells release 100-120 nm EVs that contain AAV. Nanoparticle tracking analysis provides further evidence that EVs in the 100-120 nm size range contain AAV.

Nanoparticle tracking analysis was used to evaluate the potential of HEK cells to release AAV packaged in EVs (EV-AAV) (FIG. 6). These data represent the concentration and size of EVs released from AAV-producing HEK cells. From these data we can interpret that the majority of the AAV-containing EVs are in the size range of ~100-120 nm which coincides well with electron micrographs that demonstrate successful packaging of AAV. Nanoparticle tracking analysis demonstrates two distinct size peaks. The larger peak (100-120 nm) is indicative of the size of extracellular vesicles (likely exosomes). The smaller peak is likely free AAV that is also released from the cells.

Example 5: Delivery of Proteins and mRNAs Using Extracellular Vesicles

Figure 7:
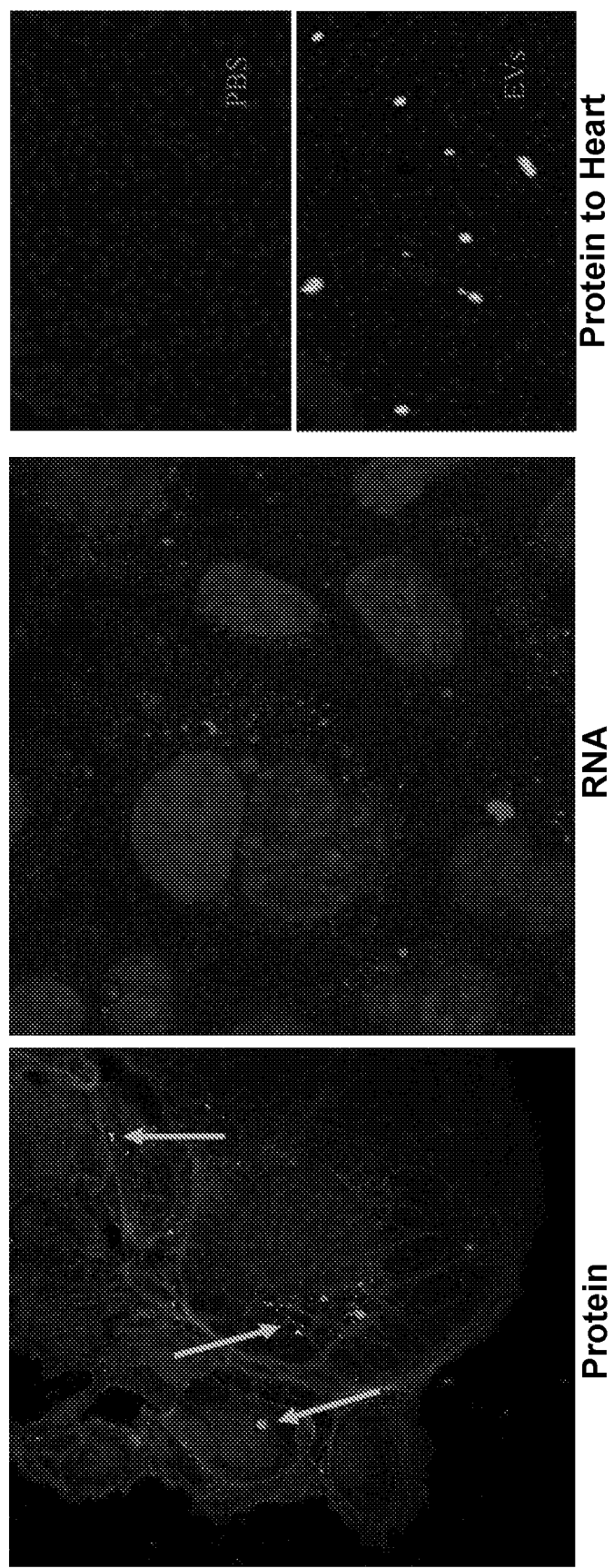
FIG. 7 shows EVs deliver protein and RNA to cardiac cells, in vitro and ex vivo. Left and middle panels: Representative images demonstrating that a low concentration of EVs ($1 \times 10^{10}$/mL) effectively delivered protein (left, green, pointed out by arrow, 63×) and RNA (right, red, 100×) into HL-1 cells. Right panels: Next, to determine the extent to which EVs could deliver protein cargo to a perfused tissue, hearts were removed from healthy mice and plumbed in a Langendorff model. This model allows the recirculation of fluid in a closed loop. Vesicle protein was labeled and hearts were perfused with PBS alone or PBS containing $1 \times 10^{11}$/mL EVs. Representative 10× images of hearts treated with PBS alone (left) or EVs with labeled protein cargo make clear that hearts readily take up vesicles.

As an example of the ability to deliver protein and mRNA to recipient muscle cells (in this case a heart cell line), HL-1 cells were treated with low concentrations of EVs ($1\times10^{10}$/ml) containing fluorescently labeled protein (FIG. 7, Left) or fluorescently labeled RNA (FIG. 7, Middle). HL-1 cells were incubated for 24 hours with EVs containing labeled protein (all protein cargo was labeled via CFSE) or RNA (Exoglow Red from Systems Bioscience). After a 24 h incubation it was found that low concentrations of EVs successfully delivered cargo to recipient cells as green-labeled protein and red-labeled RNA was apparent inside recipient cells. To directly investigate the capacity of EVs to deliver protein to the heart EVs with labeled protein cargo were added to the bath of a perfused heart using a Langendorff prep. $1 \times 10^{11}$/mL of EVs containing labeled protein (all protein cargo was labeled via CFSE) was added to the bath of a Langendorff perfused heart system for 5 minutes. In this experiment a heart was removed from a healthy mouse and tubing applied to the vena cava and aorta to allow continuous flow. Presence of protein in the heart was observed after only five minutes of perfusion, indicating the EVs rapidly deliver protein into the mouse heart (FIG. 7, Right).

Example 6: Delivery of Full Length Dystrophin Using Extracellular Vesicles

Figure 8:
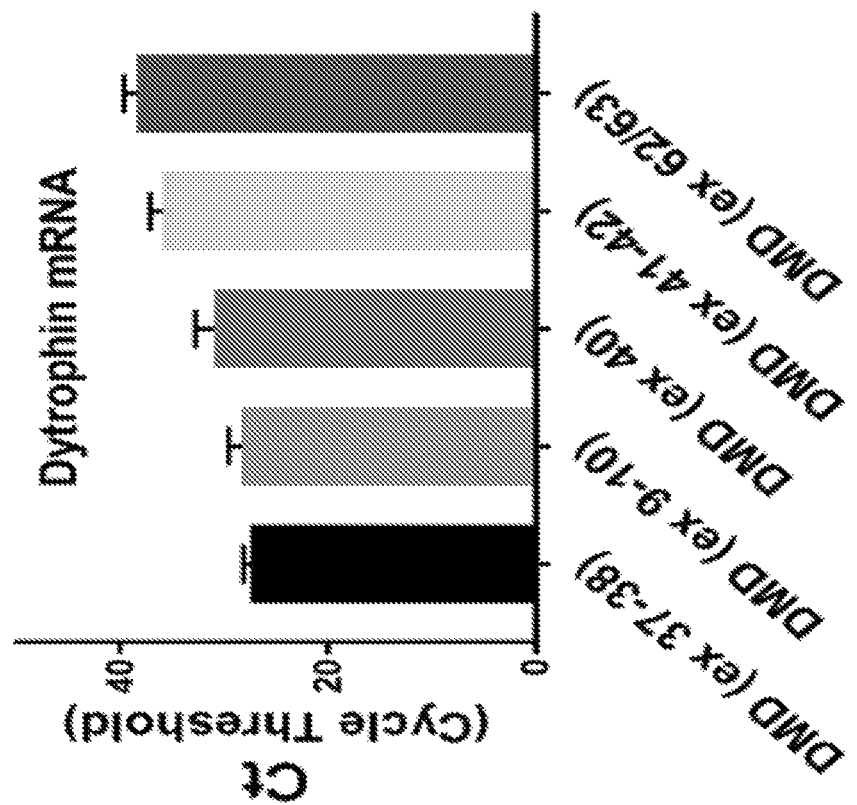
FIG. 8 shows confirmation of dystrophin positive vesicles. After packaging, vesicles were lysed and protein and mRNA collected. Left panel: Full length dystrophin protein was confirmed by detection of the full length protein by Western blot. Right panel: RNA was isolated from DEVs, cDNA was synthesized from RNA using the qScript cDNA synthesis kit (Quantabio, Beverly, MA, USA). Equal amounts of cDNA were used to perform qPCR analysis. Primers were targeted throughout the length of the dystrophin transcript.
Figure 8:
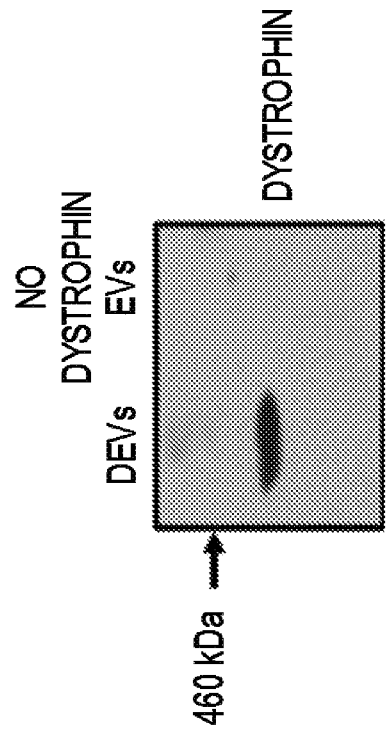

A technique has been discovered and perfected to reliably and repeatedly produce EVs containing desired protein and RNA. As an example of this approach full length dystrophin protein was packaged (DEVs), which was confirmed by Western blot (FIG. 7). Likewise, mRNA was also confirmed using directed qPCR against multiple locations along the dystrophin mRNA (FIG. 8). Implicit in this is the ability to extract protein and mRNA from vesicles at quantities suitable for these sorts of measures, which represents a significant technical hurdle and knowhow that has been overcome.

Figure 9:
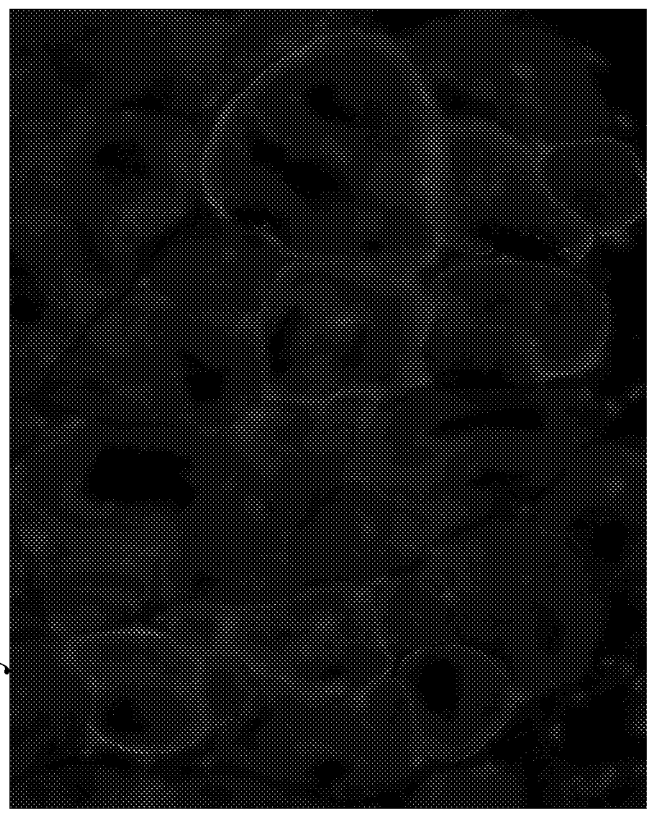
FIG. 9 shows intramuscular delivery of DEVs restores dystrophin correctly localized to the membrane. Representative images from dystrophin (red) and nuclei (blue) stained muscle following im delivery of DEVs. In these images it is apparent that a single, low dose of DEVs effectively delivered dystrophin and that dystrophin was correctly localized to the sarcolemma. Remarkably, dystrophin remained localized to the sarcolemma 20 d following a single injection of DEVs. 40 week old D2 dystrophic mice were treated with $7 \times 10^7$ DEVs in 200 μL PBS or PBS administered via intramuscular injection and euthanized after 72 hours or were similarly treated with $8.8 \times 10^9$ DEVs and were euthanized after 20 d. Muscle was visualized at 100× or 63×, respectively.
Figure 9:
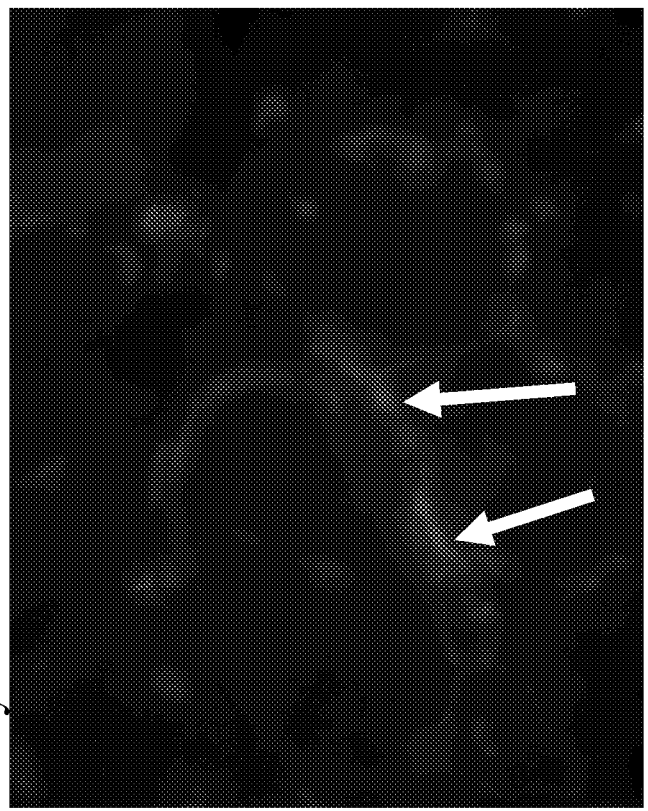
Figure 10:
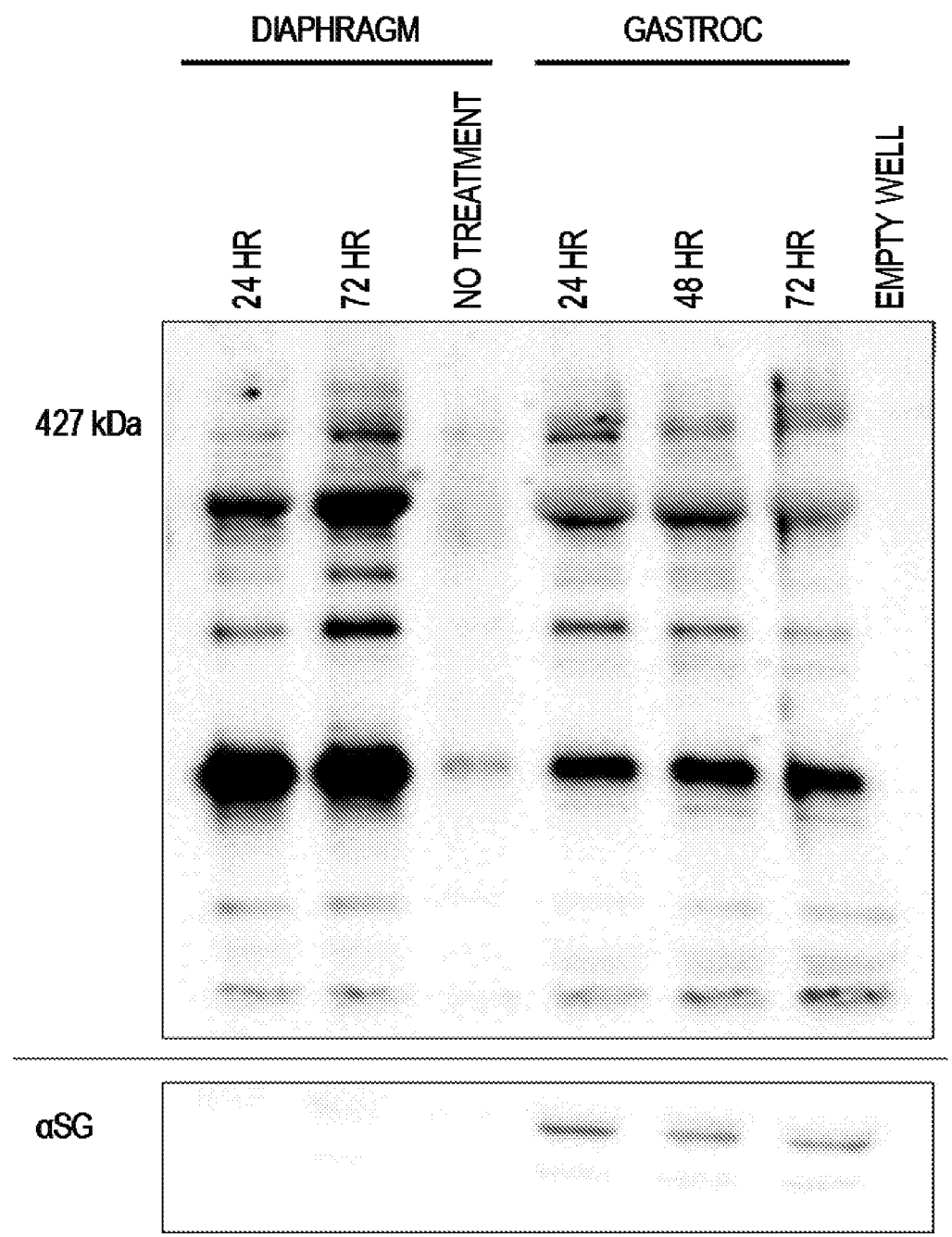
FIG. 10 shows systemic delivery of DEVs restores full length, functional dystrophin protein expression. Dystrophin deficient mice were treated with DEVs using a systemic delivery approach and muscles were collected 24-72 h later for Western blotting. Consistent with direct im injection, full length dystrophin protein was apparent in muscle from treated animals following only 24 h of exposure. Importantly, the full length band (427 kDa) is readily apparent in treated muscles. The blot was reprobed for αSG, which was also apparent in gastrocnemius muscles with trace, though greater expression that untreated muscle, in the diaphragm. That αSG was restored is suggestive of 1) functional dystrophin, 2) appropriate localization of dystrophin, 3) restoration of the dystrophin-glycoprotein complex. 40 wk old D2-mdx mice were injected with $1 \times 10^{10}$ EVs and muscles were collected 24-72 hrs later.

Given that protein and RNA can be packaged in EVs, the ability to use these EVs as a platform to deliver the intended biomolecule was demonstrated. Using DEVs as an example of this technology and approach, dystrophin was delivered to dystrophin-deficient muscle. Here, mice were injected in the triceps surae muscle group with $7 \times 10^7$ DEVS in 200 µL of PBS. After only three days it was found that this single injection of a remarkably low dose successfully delivered dystrophin to muscle cells and that dystrophin was correctly localized to the sarcolemma (FIG. 9). To gain additional insight regarding the durability of dystrophin expression and localization, this experiment was repeated with $8.8 \times 10^9$ EVs and recovered muscle following 20 d. Remarkably, 20 d after a single injection of DEVs, dystrophin protein remained localized to the sarcolemma (FIG. 9). Given the demonstrated capacity of DEVs to deliver dystrophin, in vivo, retro-orbital injection was performed in dystrophic mice with DEVs to probe the efficacy of systemic delivery. After only 24 hours dystrophin-positive muscles were found and importantly, the dystrophin was confirmed to be full length (FIG. 10); something dystrophin-deficient mice are incapable of endogenously expressing. Further, restoration of a sarcoglycan (αSG) expression was also detected (FIG. 10). In independent experiments restoration of β dystroglycan has also been shown. Dystrophin serves as they keystone for the dystrophin-glycoprotein complex (DGC) so when this protein is missing, as in DMD, the entirety of the DGC fails to assemble. That αSG protein expression is also restored by DEVs indicates not only is full length dystrophin being delivered to muscle but that dystrophin is appropriately localized to the sarcolemma (as predicted by im injections), that dystrophin is functional and able to bind to dystrophin-binding proteins, and that delivered dystrophin allows reassembly of the DGC.

Example 7: Delivery of Proteins to the Brain Using Extracellular Vesicles

Figures 11A, 11B:
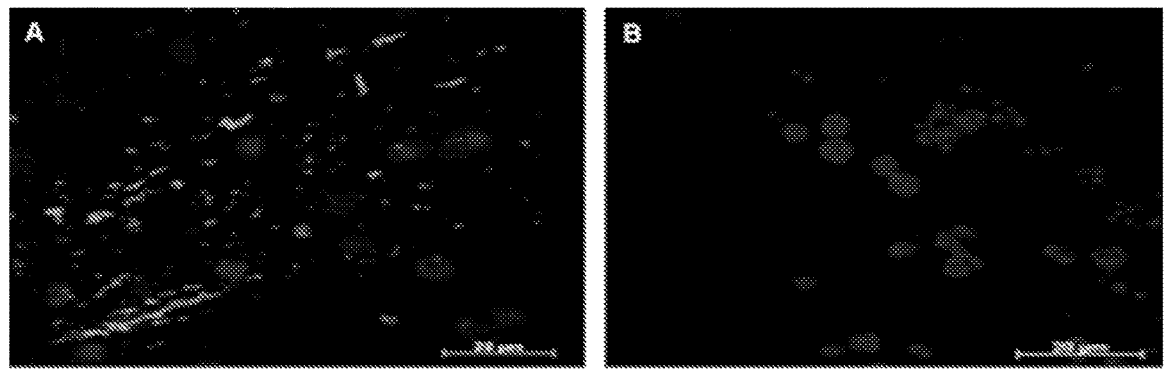
FIGS. 11A-11B show EV protein delivery to mouse brain. A) Treated mice show GFP verifying protein delivered into brain cells via EVs in vivo. B) Control (saline only administered).

EVs were isolated from HEK cell as previously described. Protein in exosomes were labeled with CFSE dye at a final concentration of 10 µm. EVs were concentrated using EXOQUICK® and $1 \times 10^{10}$ in 150 µl sterile saline injected retro-orbitally into 1.5-month old mice. 72 h later mice were euthanized, brain was removed, and embedded in OCT. Sections are 10 µm brain sections. Treated mice show GFP verifying protein delivered into brain cells via EVs in vivo (FIG. 11A) as compared to saline only controls (FIG. 11B).

Example 8: Isolation of Muscle-Derived Extracellular Vesicles

Figures 12A, 12B, 12C, 12D:
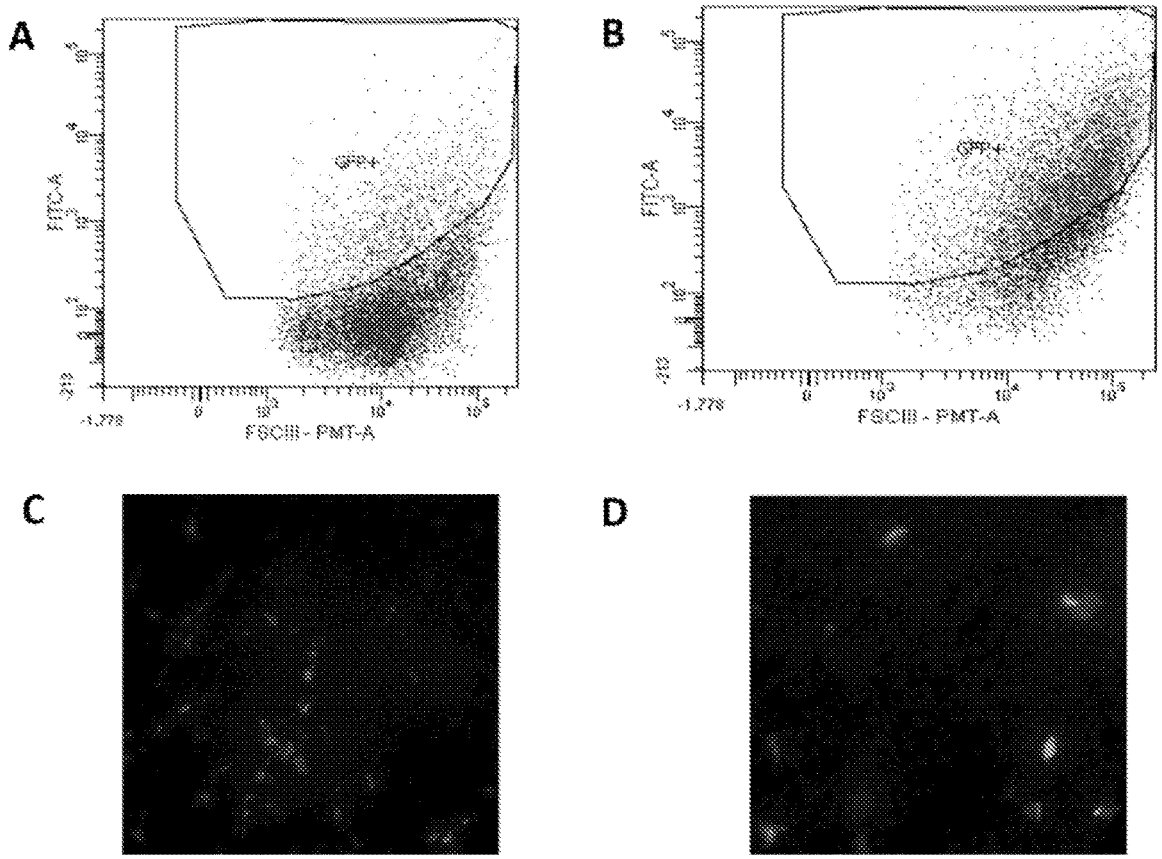
FIGS. 12A-12D show (A, C) EVs isolated from C2C12 cells or (B, D) EVs isolated from platelet-depleted human plasma.

Muscle derived EVs were isolated from fully differentiated C2C12 muscle cells (FIGS. 12A and 12C) or platelet-depleted human plasma (FIGS. 12B and 12D) by incubating with magnetic beads conjugated to a beta-sarcoglycan antibody. After isolation via magnetic separation and washing, the beads with bound muscle derived EVs were stained with CFSE, and sorted via flow cytometry (FIGS. 12A and 12B) or imaged (FIGS. 12C and 12D). GFP positive events via flow cytometry analysis verifies successful isolation from media of C2C12 cells (FIG. 12A) or human plasma (FIG. 12B) and further verified via fluorescent imaging (FIGS. 12C and 12D).

Figure 13:
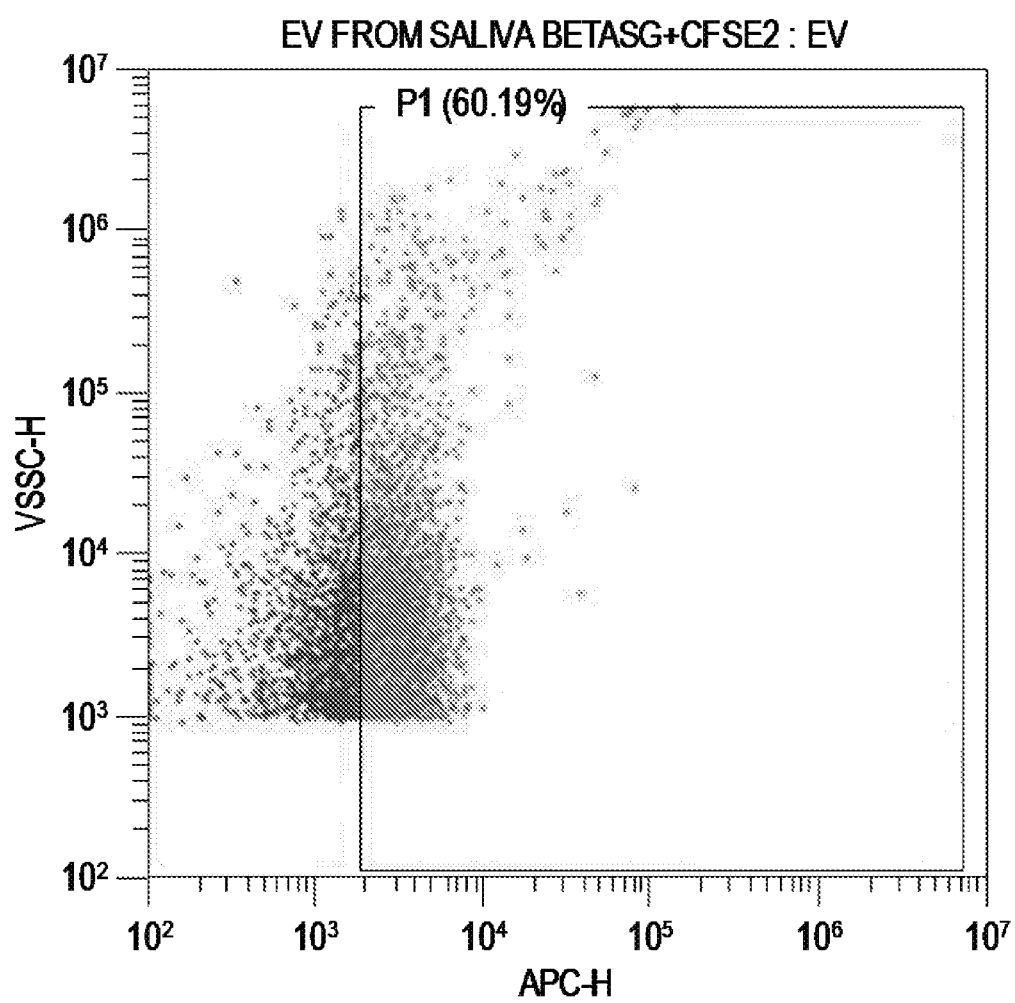
FIG. 13 shows quantification of muscle-derived EVs in saliva.

The ability to isolate muscle-derived EVs from saliva was tested. To determine the percentage of beta-sarcoglycan positive EVs in saliva, all EVs were isolated from saliva using standard methods. Subsequently, the total EV population was stained with CSFE (labeling all internal proteins with GFP) and incubated with an APC conjugated beta-sarcoglycan antibody. Samples were analyzed via flow cytometry and analyzed to determine what percentage of EVs are beta-sarcoglycan positive, and determined approximately 60% of all EVs in saliva contain beta-sarcoglycan (FIG. 13). These data verify the ability to quantify muscle-derived EVs in saliva via beta-sarcoglycan antibody.

The foregoing examples are illustrative of the present invention, and are not to be construed as limiting thereof. Although the invention has been described in detail with reference to preferred embodiments, variations and modifications exist within the scope and spirit of the invention as described and defined in the following claims.

What is claimed is:

1. A composition comprising extracellular vesicles comprising one or more therapeutic agents and/or RNA encoding the one or more therapeutic agents, the extracellular vesicles isolated from cell culture medium of cultured HEK293 or HEK293T cells comprising the one or more therapeutic agents and/or the RNA encoding the one or more therapeutic agents;

wherein the one or more therapeutic agents and/or RNA encoding the one or more therapeutic agents are endogenous to the cultured HEK293 or HEK293T cells, wherein the one or more therapeutic agents is tripartite motif-containing protein 32, utrophin, Lamin B1, Lamin A1, dystrophin, neurofibromin, tropomyosin 3, tropomyosin 2, troponin T1, selonoprotein N, sarcoglycan beta, methylmalonyl-CoA mutase, cobalamin C, lamin B2, frataxin, cofilin 2, alpha dystroglycan, contactin 1, cystic fibrosis modifier 1, bridging integrator 1, β-hexosaminidase A, acid maltase, dystrobrevin alpha, dystrobrevin beta, dystronin, or any combination thereof, wherein the cells have been modified to contain a targeting agent such that the extracellular vesicles comprise the targeting agent that targets the extracellular vesicles to muscle tissue, wherein the one or more therapeutic agents are not the targeting agent, and wherein the cultured HEK293 or HEK293T cells have not been modified to contain higher levels of the one or more therapeutic agents and/or the RNA encoding the one or more therapeutic agents.

2. The composition of claim 1, wherein the therapeutic agent is a protein.

3. The composition of claim 1, wherein the targeting agent is a transmembrane protein.

4. The composition of claim 3, wherein the targeting agent is cardiac muscle fast twitch 1 calcium-transporting ATPase, voltage-dependent calcium channel gamma subunit 1, ryanodine receptor 1, alpha-sarcoglycan, sodium-potassium transporting ATPase alpha 2 polypeptide, beta-1-syntrophin, beta-sarcoglycan, myoferlin, transmembrane protein 8C, junctional sarcoplasmic reticulum protein 1, tripartite motif containing 72, adenylosuccinate synthase like 1, cardiac muscle beta myosin heavy chain 7B, SH3 and cysteine rich domain 3, kelch-like family member 41, obscurin, cytoskeletal calmodulin and titin-interacting RhoGEF, adenylate cyclase-associated protein 2, protein kinase C and casein kinase substrate in neurons 3, junctophilin 1, junctophilin 2, reticulon 2, nicotinic cholinergic receptor alpha 1, phosphatidic acid phosphatase type 2 domain containing 3, integrin alpha-7, skeletal muscle alpha actin, actinin alpha 3, myomaker, or myomerger.

5. A composition comprising extracellular vesicles comprising one or more therapeutic agents, the extracellular vesicles isolated from cell culture medium of cultured HEK293 or HEK293T cells comprising the one or more therapeutic agents;

wherein the one or more therapeutic agents comprise viral vectors or plasmids;

wherein the cells have been modified to contain a targeting agent such that the extracellular vesicles comprise the targeting agent that targets the extracellular vessels to muscle tissue, wherein the one or more therapeutic agents are not the targeting agent, and wherein the cultured HEK293 or HEK293T cells are modified to produce the therapeutic agents.

6. The composition of claim 5, wherein the viral vector is adeno-associated virus.

7. The composition of claim 5, wherein the viral vector is lentivirus.

8. The composition of claim 5, wherein the one or more therapeutic agents have been introduced into the cells.

9. The composition of claim 8, wherein the one or more therapeutic agents have been introduced into the cells by transfection, transduction, infection, electroporation, or any combination thereof.

10. The composition of claim 5, wherein the targeting agent is a transmembrane protein.

11. The composition of claim 10, wherein the targeting agent is cardiac muscle fast twitch 1 calcium-transporting ATPase, voltage-dependent calcium channel gamma subunit 1, ryanodine receptor 1, alpha-sarcoglycan, sodium-potassium transporting ATPase alpha 2 polypeptide, beta-1-syntrophin, beta-sarcoglycan, myoferlin, transmembrane protein 8C, junctional sarcoplasmic reticulum protein 1, tripartite motif containing 72, adenylosuccinate synthase like 1, cardiac muscle beta myosin heavy chain 7B, SH3 and cysteine rich domain 3, kelch-like family member 41, obscurin, cytoskeletal calmodulin and titin-interacting RhoGEF, adenylate cyclase-associated protein 2, protein kinase C and casein kinase substrate in neurons 3, junctophilin 1, junctophilin 2, reticulon 2, nicotinic cholinergic receptor alpha 1, phosphatidic acid phosphatase type 2 domain containing 3, integrin alpha-7, skeletal muscle alpha actin, actinin alpha 3, myomaker, or myomerger.

* * * * *